United States Patent
Hung et al.

(10) Patent No.: US 10,843,189 B2
(45) Date of Patent: Nov. 24, 2020

(54) METHODS AND APPARATUS FOR CELL CULTURE ARRAY

(71) Applicant: THE REGENTS OF THE UNIVERSITY OF CALIFORNIA, Oakland, CA (US)

(72) Inventors: Paul J. Hung, Berkeley, CA (US); Philip J. Lee, Alameda, CA (US); Luke P. Lee, Orinda, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 138 days.

(21) Appl. No.: 15/925,445

(22) Filed: Mar. 19, 2018

(65) Prior Publication Data

US 2019/0106664 A1    Apr. 11, 2019

Related U.S. Application Data

(60) Continuation of application No. 14/855,584, filed on Sep. 16, 2015, now Pat. No. 9,969,963, which is a
(Continued)

(51) Int. Cl.
*B01L 3/00* (2006.01)
*C12M 1/00* (2006.01)
(Continued)

(52) U.S. Cl.
CPC ... *B01L 3/502707* (2013.01); *B01L 3/502715* (2013.01); *B01L 3/502746* (2013.01); *B01L 3/502761* (2013.01); *C12M 21/08* (2013.01); *C12M 23/16* (2013.01); *C12M 23/34* (2013.01); *C12M 29/06* (2013.01); *C12M 29/10* (2013.01); *C12M 41/46* (2013.01); *C12N 5/0602* (2013.01); *B01L 2200/027* (2013.01);
(Continued)

(58) Field of Classification Search
None
See application file for complete search history.

(56) References Cited

U.S. PATENT DOCUMENTS 4,055,613 A    10/1977 Kapral
4,661,455 A    4/1987 Hubbard
(Continued)

FOREIGN PATENT DOCUMENTS

DE    19948087    5/2001
EP    0155237     9/1995
(Continued)

OTHER PUBLICATIONS

P.J. Hung et al., A Novel High Aspect Ratio Microfluidic Design to Provide a Stable and Uniform Microenvirnment for Cell Growth in a High Throuput Mammalian Cell Culture Array, Lap Chip, 2005, 5, 44-48, published online on Nov. 2, 2004. (Year: 2004).*
(Continued)

*Primary Examiner* — Jiong-Ping Lu
(74) *Attorney, Agent, or Firm* — O'Banion & Ritchey LLP; John P. O'Banion

(57) ABSTRACT

Methods and systems are described for improved handling and/or culturing and/or assaying of cells, chemically active beads, or similar materials in microfluidic systems and microfluidic culture arrays.

6 Claims, 26 Drawing Sheets

Related U.S. Application Data division of application No. 11/994,997, filed as application No. PCT/US2006/026364 on Jul. 6, 2006, now Pat. No. 9,260,688.

(60) Provisional application No. 60/773,467, filed on Feb. 14, 2006, provisional application No. 60/697,449, filed on Jul. 7, 2005.

(51) Int. Cl.
  *C12M 3/06* (2006.01)
  *C12M 3/00* (2006.01)
  *C12M 1/34* (2006.01)
  *C12N 5/071* (2010.01)

(52) U.S. Cl.
  CPC ............... *B01L 2200/0647* (2013.01); *B01L 2200/0689* (2013.01); *B01L 2300/0627* (2013.01); *B01L 2300/0816* (2013.01); *B01L 2400/0487* (2013.01); *B01L 2400/086* (2013.01); *B01L 2400/088* (2013.01); *B81B 2201/05* (2013.01); *B81B 2201/06* (2013.01); *B81C 2201/019* (2013.01)

(56) References Cited

U.S. PATENT DOCUMENTS

| | | |
|---|---|---|
| 4,734,373 A | 3/1988 | Bartal |
| 4,748,124 A | 5/1988 | Volger |
| 5,079,168 A | 1/1992 | Amiot |
| 5,153,131 A | 10/1992 | Wolf et al. |
| 5,310,676 A | 5/1994 | Johansson et al. |
| 5,330,908 A | 7/1994 | Spaulding et al. |
| 5,376,252 A | 12/1994 | Ekstrom et al. |
| 5,416,022 A | 5/1995 | Amiot |
| 5,424,209 A | 6/1995 | Kearney |
| 5,437,998 A | 8/1995 | Schwarz et al. |
| 5,451,524 A | 9/1995 | Coble et al. |
| 5,462,874 A | 10/1995 | Wold et al. |
| 5,565,353 A | 10/1996 | Klebe et al. |
| 5,589,112 A | 12/1996 | Spaulding |
| 5,593,814 A | 1/1997 | Matsuda et al. |
| 5,602,028 A | 1/1997 | Minchinton |
| 5,627,070 A | 5/1997 | Gruenberg |
| 5,637,469 A | 6/1997 | Wilding et al. |
| 5,641,644 A | 6/1997 | Klebe |
| 5,658,797 A | 8/1997 | Bader |
| 5,686,301 A | 11/1997 | Falkenberg et al. |
| 5,686,304 A | 11/1997 | Codner |
| 5,693,537 A | 12/1997 | Wilson et al. |
| 5,702,941 A | 12/1997 | Schwarz |
| 5,714,384 A | 2/1998 | Wilson et al. |
| 5,763,261 A | 6/1998 | Gruenberg |
| 5,763,275 A | 6/1998 | Nagels et al. |
| 5,763,279 A | 6/1998 | Schwarz et al. |
| 5,786,215 A | 7/1998 | Brown et al. |
| 5,793,440 A | 8/1998 | Nakasaka et al. |
| 5,801,054 A | 9/1998 | Kiel et al. |
| 5,866,345 A | 2/1999 | Wilding et al. |
| 5,882,918 A | 3/1999 | Goffe |
| 5,900,361 A | 5/1999 | Klebe |
| 5,912,177 A | 6/1999 | Turner et al. |
| 5,924,583 A | 7/1999 | Stevens et al. |
| 5,932,315 A | 8/1999 | Lum et al. |
| 5,942,443 A | 8/1999 | Parce et al. |
| 6,039,897 A | 3/2000 | Lochhead et al. |
| 6,048,498 A | 4/2000 | Kennedy |
| 6,096,532 A | 8/2000 | Armstrong et al. |
| 6,107,085 A | 8/2000 | Coughlin et al. |
| 6,153,073 A | 11/2000 | Dubro et al. |
| 6,190,913 B1 | 2/2001 | Singh |
| 6,197,575 B1 | 3/2001 | Griffith et al. |
| 6,228,635 B1 | 5/2001 | Armstrong et al. |
| 6,238,908 B1 | 5/2001 | Armstrong et al. |
| 6,251,343 B1 | 6/2001 | Dubrow et al. |
| 6,274,337 B1 | 8/2001 | Parce et al. |
| 6,277,642 B1 | 8/2001 | Mentzen et al. |
| 6,297,046 B1 | 10/2001 | Smith et al. |
| 6,323,022 B1 | 11/2001 | Chang et al. |
| 6,326,211 B1 | 12/2001 | Anderson et al. |
| 6,403,369 B1 | 6/2002 | Wood |
| 6,410,309 B1 | 6/2002 | Barbera-Guillem et al. |
| 6,455,310 B1 | 9/2002 | Barbera-Guillem |
| 6,465,243 B2 | 10/2002 | Okada et al. |
| 6,468,792 B1 | 10/2002 | Bader |
| 6,481,648 B1 | 11/2002 | Zimmermann |
| 6,495,104 B1 | 12/2002 | Unno et al. |
| 6,518,035 B1 | 2/2003 | Ashby et al. |
| 6,534,013 B1 | 3/2003 | Kennedy |
| 6,548,263 B1 | 4/2003 | Kapur et al. |
| 6,551,841 B1 | 4/2003 | Wilding et al. |
| 6,555,365 B2 | 4/2003 | Barbera-Guillem et al. |
| 6,562,616 B1 | 5/2003 | Toner et al. |
| 6,569,675 B2 | 5/2003 | Wall et al. |
| 6,576,458 B1 | 6/2003 | Sarem et al. |
| 6,585,939 B1 | 7/2003 | Dapprich |
| 6,593,136 B1 | 7/2003 | Geiss |
| 6,637,463 B1 | 10/2003 | Lei |
| 6,648,015 B1 | 11/2003 | Chow |
| 6,653,124 B1 | 11/2003 | Freeman |
| 6,673,595 B2 | 1/2004 | Barbera-Guillem |
| 6,756,019 B1 | 6/2004 | Dubrow et al. |
| 6,759,245 B1 | 7/2004 | Toner et al. |
| 6,794,184 B1 | 9/2004 | Mohr et al. |
| 6,811,752 B2 | 11/2004 | Barbera-Guillem |
| 6,821,772 B2 | 11/2004 | Barbera-Guillem et al. |
| 6,846,668 B1 | 1/2005 | Garman et al. |
| 6,857,449 B1 | 2/2005 | Chow |
| 6,908,767 B2 | 6/2005 | Bader |
| 6,915,679 B2 | 7/2005 | Chien et al. |
| 6,969,166 B2 | 11/2005 | Clark et al. |
| 7,005,292 B2 | 2/2006 | Wilding et al. |
| 7,018,830 B2 | 3/2006 | Wilding et al. |
| 7,022,518 B1 | 4/2006 | Feye |
| 7,067,263 B2 | 6/2006 | Parce et al. |
| 7,141,386 B2 | 11/2006 | Dunfield et al. |
| 7,155,344 B1 | 12/2006 | Parce et al. |
| 7,160,687 B1 | 1/2007 | Kapur et al. |
| 7,171,983 B2 | 2/2007 | Chien et al. |
| 7,192,769 B2 | 3/2007 | Pykett et al. |
| 7,223,371 B2 | 5/2007 | Hayenga et al. |
| 7,343,248 B2 | 3/2008 | Parce et al. |
| 7,745,209 B2 | 6/2010 | Martin et al. |
| 7,919,319 B2 | 4/2011 | Jervis |
| 9,260,688 B2 | 2/2016 | Hung et al. |
| 2002/0039785 A1 | 4/2002 | Schroeder et al. |
| 2002/0053399 A1* | 5/2002 | Soane ............... B01L 3/502707 156/292 |
| 2002/0108660 A1 | 8/2002 | Staats |
| 2002/0110905 A1 | 8/2002 | Barbera-Guillem et al. |
| 2002/0177221 A1 | 11/2002 | Nishiguchi et al. |
| 2003/0008388 A1 | 1/2003 | Barbera-Guillem et al. |
| 2003/0008389 A1 | 1/2003 | Carll |
| 2003/0030184 A1 | 2/2003 | Kim |
| 2003/0040104 A1 | 2/2003 | Barbera-Guillem |
| 2003/0124623 A1 | 7/2003 | Yager et al. |
| 2003/0143727 A1 | 7/2003 | Chang |
| 2003/0156992 A1 | 8/2003 | Anderson et al. |
| 2003/0211012 A1 | 11/2003 | Bergstrom et al. |
| 2004/0029266 A1 | 2/2004 | Barbera-Guillem |
| 2004/0043481 A1 | 3/2004 | Wilson |
| 2004/0072278 A1 | 4/2004 | Chou |
| 2004/0096960 A1 | 5/2004 | Mehta et al. |
| 2004/0132175 A1 | 7/2004 | Vetillard et al. |
| 2004/0202579 A1 | 10/2004 | Larsson et al. |
| 2004/0229349 A1 | 11/2004 | Daridon |
| 2004/0238484 A1* | 12/2004 | Le Pioufle ............ B01J 19/0093 216/27 |
| 2005/0009179 A1 | 1/2005 | Gemmiti et al. |
| 2005/0019213 A1 | 1/2005 | Kechagia et al. |
| 2005/0032208 A1 | 2/2005 | Oh et al. |
| 2005/0072946 A1 | 4/2005 | Studer et al. |
| 2005/0101009 A1 | 5/2005 | Wilson et al. |

(56) References Cited

U.S. PATENT DOCUMENTS

| | | |
|---|---|---|
| 2005/0106717 A1 | 5/2005 | Wilson et al. |
| 2005/0169962 A1 | 8/2005 | Bhatia et al. |
| 2005/0214173 A1 | 9/2005 | Facer et al. |
| 2005/0221373 A1 | 10/2005 | Enzelberger |
| 2005/0260745 A1 | 11/2005 | Domansky et al. |
| 2005/0266582 A1 | 12/2005 | Modlin |
| 2006/0003436 A1 | 1/2006 | DiMilla et al. |
| 2006/0031955 A1 | 2/2006 | West et al. |
| 2006/0112438 A1 | 5/2006 | West et al. |
| 2006/0121606 A1 | 6/2006 | Ito et al. |
| 2006/0136182 A1 | 6/2006 | Vacanti et al. |
| 2006/0141617 A1 | 6/2006 | Desai et al. |
| 2006/0154361 A1 | 7/2006 | Wikswo et al. |
| 2006/0166354 A1 | 7/2006 | Wikswo |
| 2006/0199260 A1 | 9/2006 | Zhang et al. |
| 2007/0026516 A1 | 2/2007 | Martin et al. |
| 2007/0084706 A1 | 4/2007 | Takayama et al. |
| 2007/0090166 A1 | 4/2007 | Takayama et al. |
| 2007/0122314 A1 | 5/2007 | Strand |
| 2007/0264705 A1 | 11/2007 | Dodgson |
| 2007/0275455 A1 | 11/2007 | Hung et al. |
| 2008/0085556 A1 | 4/2008 | Graefing et al. |
| 2008/0176318 A1 | 7/2008 | Wilson et al. |
| 2008/0227176 A1 | 9/2008 | Wilson et al. |
| 2008/0233607 A1 | 9/2008 | Yu et al. |
| 2009/0023608 A1 | 1/2009 | Hung et al. |
| 2009/0203126 A1 | 8/2009 | Hung et al. |

FOREIGN PATENT DOCUMENTS

| | | |
|---|---|---|
| EP | 0725134 | 8/1996 |
| EP | 0890636 | 1/1999 |
| GB | 1539263 | 1/1979 |
| WO | 1991015570 | 10/1991 |
| WO | 2000056870 | 9/2000 |
| WO | 2000060352 | 10/2000 |
| WO | 2000078932 | 10/2000 |
| WO | 2001092462 | 12/2001 |
| WO | 2003085080 | 10/2003 |
| WO | 2004059299 | 7/2004 |
| WO | 2004106484 | 12/2004 |
| WO | 2005023124 A2 | 3/2005 |
| WO | 2005035728 | 4/2005 |
| WO | 2007008609 | 1/2007 |
| WO | 2009089189 A2 | 7/2009 |
| WO | 2003098218 | 11/2013 |

OTHER PUBLICATIONS

Ong et al., "A gel-free 3D microfluidic cell culture system", Biomaterials, vol. 29, No. 22, 2008, pp. 3237-3244, published online May 2, 2008.
European Patent Office (EPO), "The extended European search report", dated Apr. 3, 2012, related EP Patent Application No. 06786499.1, pp. 1-7.
Chang et al., "Fabrication of polymer microlens arrays using capillary forming with a soft mold of microholes array and UV-curable polymer", Optical Society of America, Optics Express, vol. 14, No. 13, Jun. 26, 2006, pp. 6253-6258.
Chao et al., "Rapid frabrication of microchannels using microscale plasma activated templating (PLAT) generating water molds", The Royal Society of Chemistry, Lab on a Chip, vol. 7, 2007, pp. 641-643, published online Apr. 5, 2007.
Degenaar et al., "A Method of Micrometer Resolution Patterning of Primary Culture Neurons for SPM Analysis", The Japanese Biochemical Society, J. Biochem., vol. 130, 2001, pp. 367-376.
Lim et al., "Fabrication of Microfluidic Mixers and Artifical Vasculatures Using a High-Brightness Diode-Pumped Nd: YAG Laser Direct Write Method", The Royal Society of Chemistry, Lab on a Chip, vol. 3, 2003, pp. 318-323, published online Oct. 13, 2003.
Runyon et al., "Minimal Functional Model of Hemistasis in a Biomimetic Microfluidic System", Amgew. Chem. Intl. Ed. 2004, 43: 1531-1536.
Tan et al., "Microfludic Patterning of Cellular Biopolymer Matrices for Biomimetic 3-D structures", Kluwer Academic Publishers, Biomedical Microdevices 5:3, 235-244, 2003.
Hung et al., "Declaration under 37 CFR 1.132 as to the inventionship of the disclosed and claimed subject invention in relation to the co-authors of a reference publication", Jun. 18, 2014, related U.S. Appl. No. 11/994,997, 10 pages.
European Patent Office (EPO), "The extended European search report", dated Apr. 13, 2016, pp. 1-6, with claims searched, pp. 7-10.
Hung et al., "A novel high aspect ratio microfluidic design to provide a stable and uniform microenvironment for cell growth in a high throughput mammalian cell culture array", Lab on a Chip, Vo. 5, 2005, pp. 44-48, published online Nov. 2, 2004.
European Patent Office (EPO), Office Action dated Jul. 10, 2015, related EP application No. 06786499.1 (pp. 1-4), with claims examined (pp. 5-7).
ISA/US, International Search Report and Written Opinion, dated Apr. 9, 2008, related PCT International Patent Application No. PCT/US2006/026364, (pp. 1-9), claims searched (pp. 10-16).
CellASIC Corporation, "ONIX Application Note: Microincubator for Long Term Live Cell Microscopy", Feb. 3, 2012, pp. 1-4.
Hung et al., "Continuous Perfusion Microfludic Cell Culture Array for High-Throughput Cell-Based Assays", Biotechnology and Bioengineering, vol. 89, No. 1, Jan. 5, 2005, pp. 1-8, published online Dec. 3, 2004.
Lee et al., "Dynamic cell culture: a microfluidic function generator for live cell microscopy", The Royal Society of Chemistry, Lab on a Chip, vol. 9, No. 1, 2009, published online Oct. 20, 2008, pp. 164-166.
Lee et al., "Microfluidic System for Automated Cell-Based Assays", Journal of Laboratory Automation, 12(6): 363-367, Dec. 2007.
Brinkhof Bas, et al., "Meet the Stem Cells, Production of Cultured Wheat from a Stem Cell Biology Perspective", Engineering Aspects of Food Biotechnology, Ch5, 2004, pp. 111-142.
Chung, Bong Geun, et al. "Human neural stem cell growth and differentiation in a gradient-generating microfluidic device", Lab Chip, 2005, vol. 5 No. 4, published online Mar. 9, 2005, pp. 401-406.
European Patent Office (EPO), Communication pursuant to Article 94(3) EPC dated Dec. 4, 2017, related European application No. EP 16 150 645.6, pp. 1-4, with claims examined, pp. 5-8.

* cited by examiner

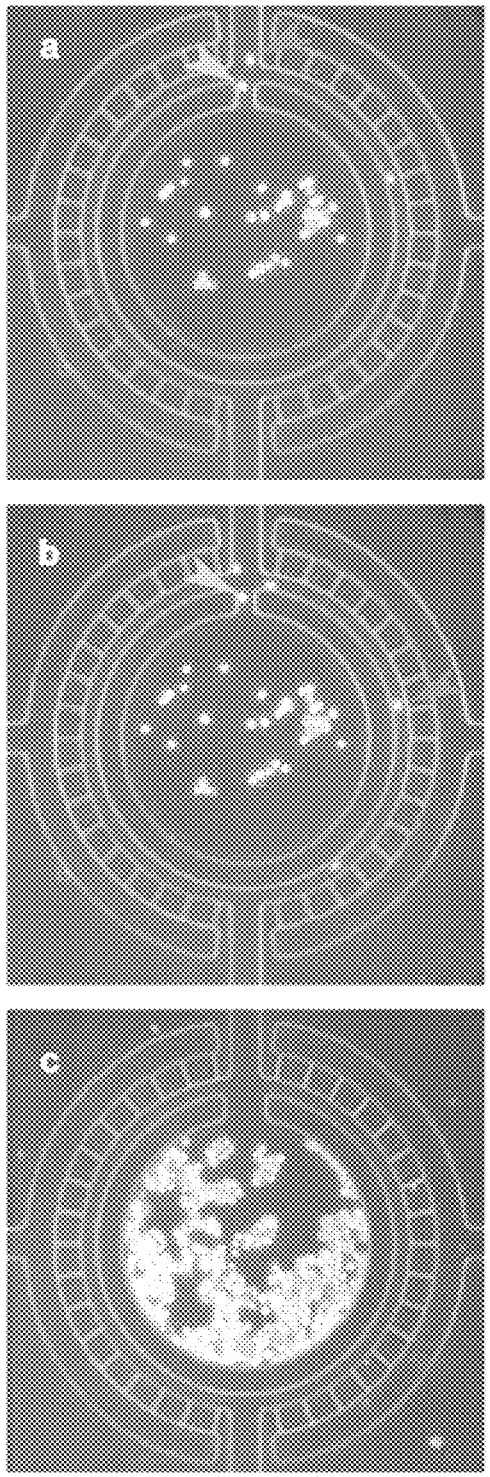
*FIG. 4A-C*

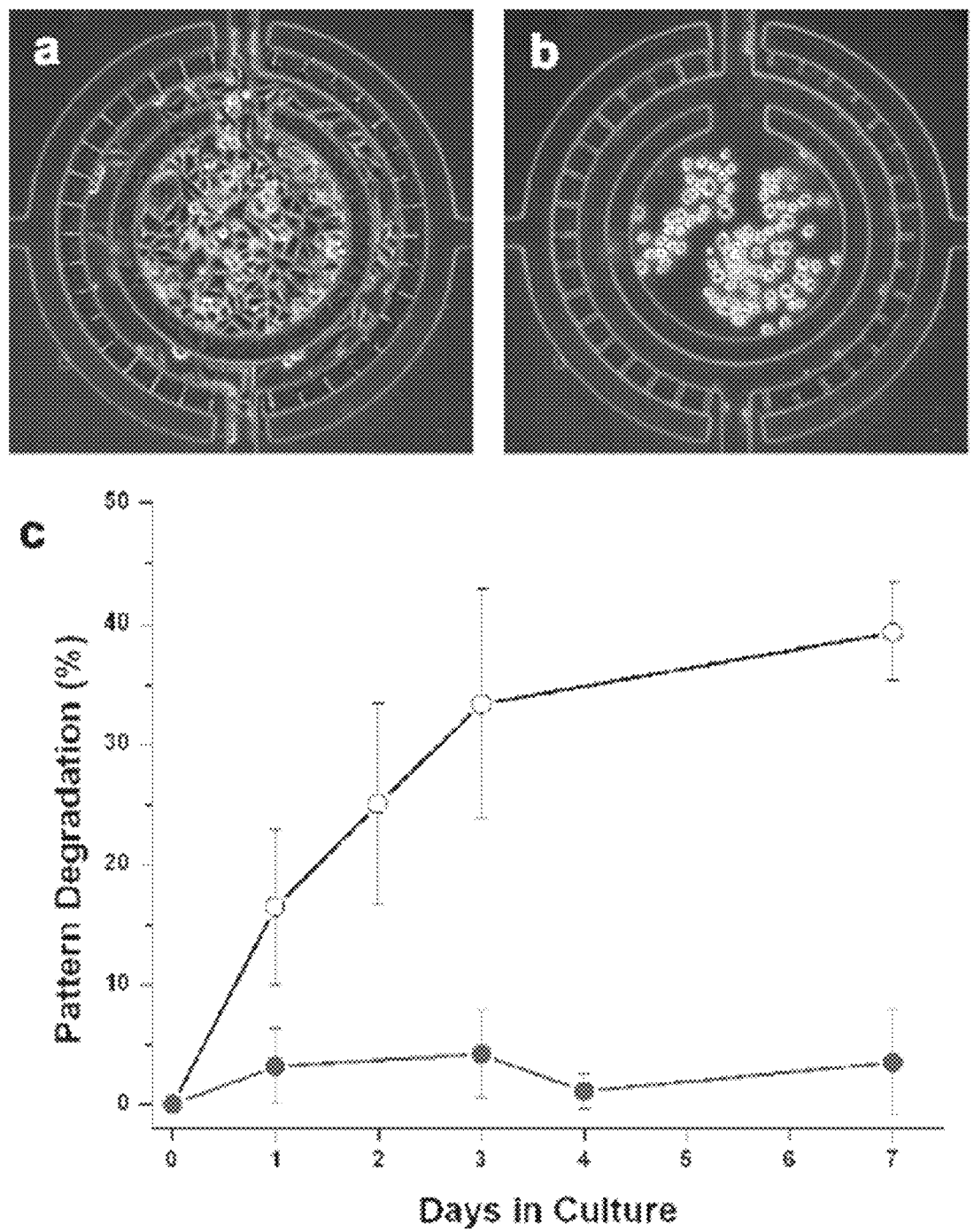
FIG. 5A-C

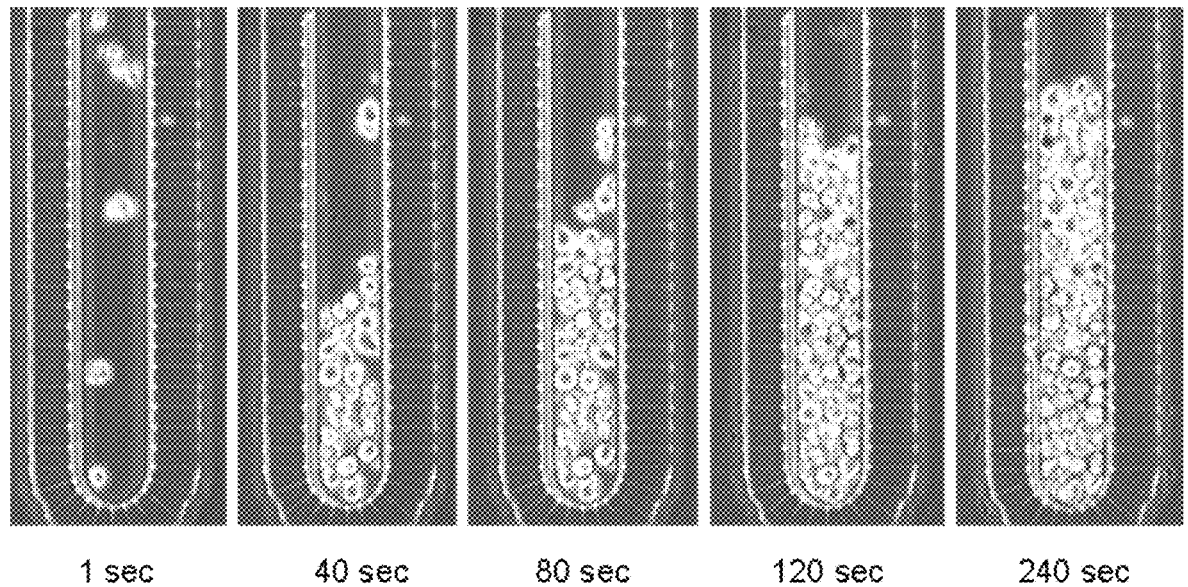
| 1 sec | 40 sec | 80 sec | 120 sec | 240 sec |
*FIG. 10A*
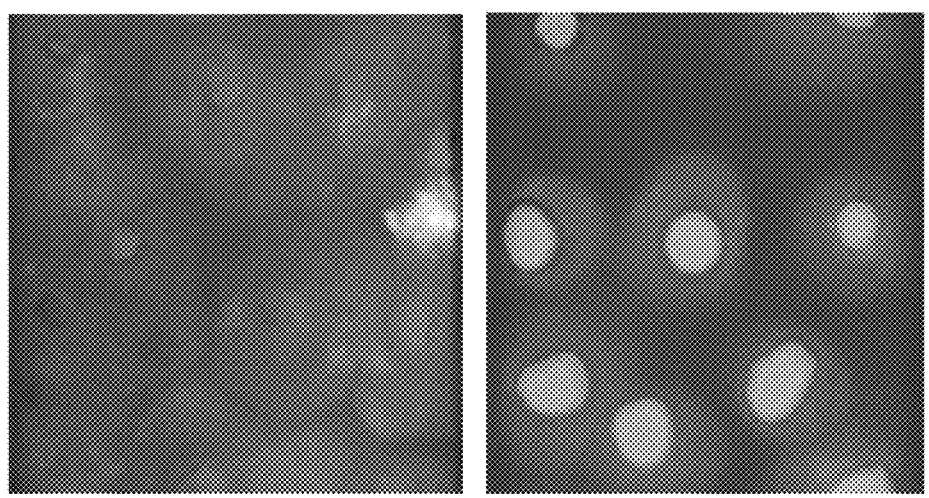
*FIG. 10B-C*

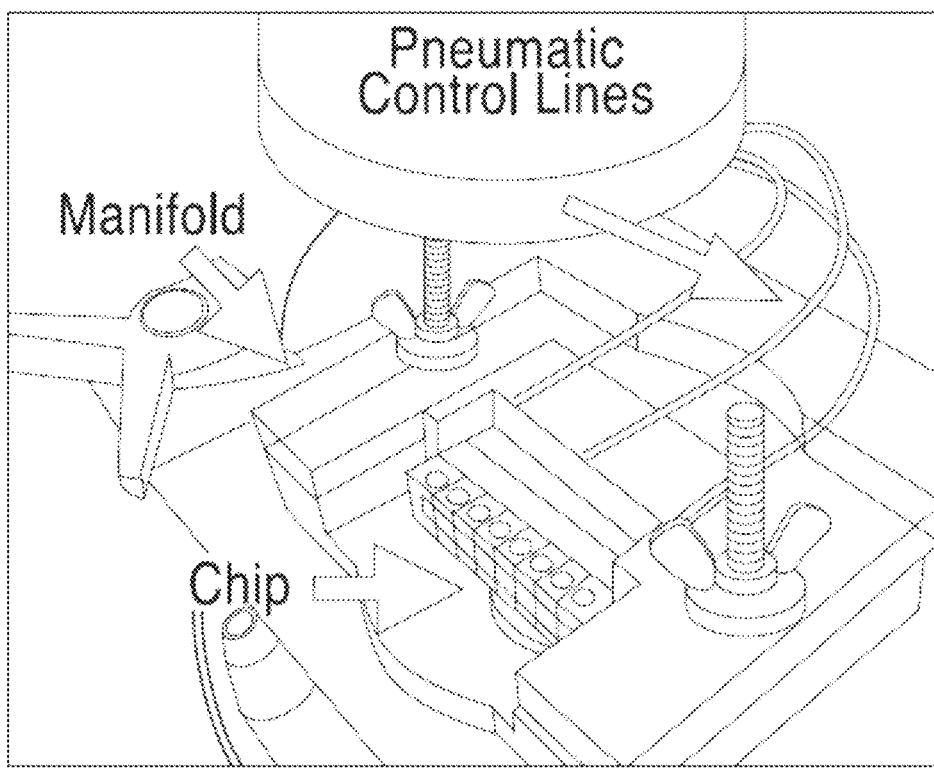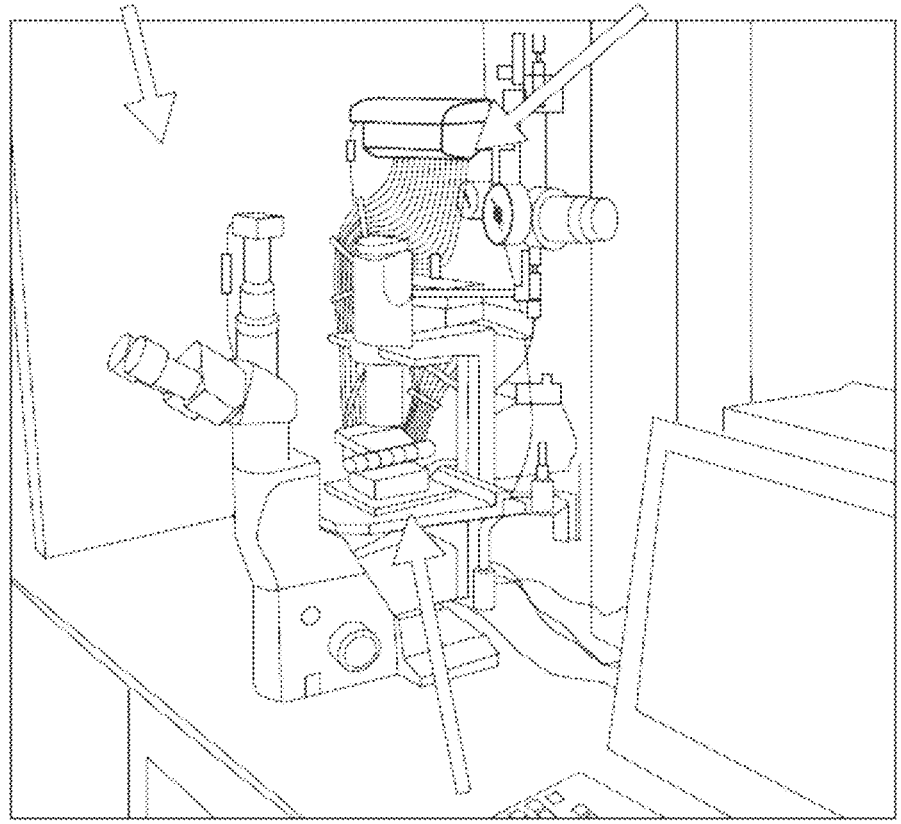
*FIG. 21*

Retrieve all plastic plate

Spin coat thin adhesive (biocompatible) on another plastic sheet

Press bonding of two pieces

| Disease Classification | Disease |
|---|---|
| Cardiovascular Disease | Atherosclerosis; Unstable angina; Myocardial Infarction; Restenosis after angioplasty or other percutaneous intervention; Congestive Heart Failure; Myocarditis; Endocarditis; Endothelial Dysfunction; Cardiomyopathy |
| Endocrine Disease | Diabetes Mellitus I and II; Thyroiditis; Addisson's Disease |
| Infectious Disease | Hepatitis A, B, C, D, E; Malaria; Tuberculosis; HIV; Pneumocystis Carinii; Giardia; Toxoplasmosis; Lyme Disease; Rocky Mountain Spotted Fever; Cytomegalovirus; Epstein Barr Virus; Herpes Simplex Virus; Clostridium Dificile Colitis; Meningitis (all organisms); Pneumonia (all organisms); Urinary Tract Infection (all organisms); Infectious Diarrhea (all organisms) |
| Angiogenesis | Pathologic angiogenesis; Physiologic angiogenesis; Treatment induced angiogenesis |
| Inflammatory/Rheumatic Disease | Rheumatoid Arthritis; Systemic Lupus Erythematosis; Sjogrens Disease; CREST syndrome; Scleroderma; Ankylosing Spondylitis; Crohn's; Ulcerative Colitis; Primary Sclerosing Cholangitis; Appendicitis; Diverticulitis; Primary Biliary Sclerosis; Wegener's Granulomatosis; Polyarteritis nodosa; Whipple's Disease; Psoriasis; Microscopic Polyanngiitis; Takayasu's Disease; Kawasaki's Disease; Autoimmune hepatitis; Asthma; Churg-Strauss Disease; Beurger's Disease; Raynaud's Disease; Cholecystitis; Sarcoidosis; Asbestosis; Pneumoconioses |
| Transplant Rejection | Heart; Lung; Liver; Pancreas; Bowel; Bone Marrow; Stem Cell; Graft versus host disease; Transplant vasculopathy |
| Leukemia and Lymphoma | |

*FIG. 25. (TABLE 1)*

METHODS AND APPARATUS FOR CELL CULTURE ARRAY

CROSS REFERENCE TO RELATED APPLICATIONS

This application is a continuation of U.S. patent application Ser. No. 14/855,584 filed on Sep. 16, 2015, incorporated herein by reference in its entirety, which is a division of U.S. patent application Ser. No. 11/994,997 filed on Aug. 11, 2008, now U.S. Pat. No. 9,260,688 issued on Feb. 16, 2016, incorporated herein by reference in its entirety, which is a 35 U.S.C. § 371 national stage completion of, and claims priority to, PCT international application number PCT/US2006/026364 filed on Jul. 6, 2006, incorporated herein by reference in its entirety, which claims priority to, and the benefit of, U.S. provisional patent application Ser. No. 60/773,467 filed on Feb. 14, 2006, incorporated herein by reference in its entirety, and which also claims priority to, and the benefit of, U.S. provisional patent application Ser. No. 60/697,449 filed on Jul. 7, 2005, incorporated herein by reference in its entirety. Priority is claimed to each of the foregoing applications.

STATEMENT REGARDING FEDERALLY SPONSORED RESEARCH OR DEVELOPMENT

This invention was made with Government support under N00014-03-1-0808, awarded by the Office of Naval Research, and under BES-0239333, awarded by the National Science Foundation. The Government has certain rights in the invention.

COPYRIGHT NOTICE

Pursuant to 37 C.F.R. 1.71(e), applicants note that a portion of this disclosure contains material that is subject to copyright protection (such as, but not limited to, diagrams, device photographs, or any other aspects of this submission for which copyright protection is or may be available in any jurisdiction). The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The invention in specific embodiments relates generally to molecular and cellular sample preparation and/or culturing and/or analysis and more particularly to micro structures useful therewith. In further specific embodiments, the invention involves methods, systems, and/or devices for culturing and/or assaying cells and/or other biologically or chemically active materials using a novel culture structure, array, method or chamber. In other embodiments, the present invention relates to methods and/or system and/or apparatus enabling the culturing of cells in a configuration allowing for simulating living tissues and/or organs and/or solid tumors, such as systems for an artificial liver, kidney, pancreas, thyroid, etc. In specific embodiments, the invention involves methods and/or system and/or apparatus involving various structures for manipulating objects, such as cells or beads, in a fluidic medium and optionally performing certain analysis or observations thereof or deriving materials produced from biologic cultures.

BACKGROUND OF THE INVENTION

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

High quality molecular and cellular sample preparations are the foundation for effective technology validation as well as for meaningful biological and clinical research and for various clinical and other applications. In vitro samples that closely represent their in vivo characteristics could potentially benefit a wide range of molecular and cellular applications. Handling, characterization, culturing, and visualization of cells or other biologically or chemically active materials (such as beads coated with various biological molecules) has become increasingly valued in the fields of drug discovery, disease diagnoses and analysis, and a variety of other therapeutic and experimental work.

Mammalian cell culture is an essential aspect of medical and biological research and development and ultimately treatment. However, most current practices are labor/resource intensive, not amenable to process control, cannot address cellular length scales, and prevent long-term continuous real-time monitoring or observation. Furthermore, current cell culture practices have not provided fully satisfactory solutions to the challenges of maintaining effective solid aggregates of cells in culture.

Advances have been made by combining microfabrication and microfluidic technologies with cell culture during the past decade; nevertheless, there is not yet a compact device effectively providing the same functionality as traditional cell culture.

Some recent publications and/or patent documents that discuss various strategies related to cell culture using microfluidic systems and related activities include the following U.S. patent applications and non-patent literature, which, along with all citations therein, are incorporated herein by reference to provide background. A listing of these references here does not indicate the references constitute prior art.

Cytoplex, Inc. U.S. Pat. No. 6,653,124 "Array-based microenvironment for cell culturing, cell monitoring and drug-target validation."

Cellomics, Inc. U.S. Pat. No. 6,548,263 "Miniaturized cell array methods and apparatus for cell-based screening."

Fluidigm, Inc. Published Application 20040229349 (Nov. 18, 2004) "Microfluidic particle-analysis systems."

OTHER REFERENCES I

1. T. H. Park and M. L. Shuler, *Biotechnol. Prog.*, 2003, 19, 243.
2. G. M. Walker, H. C. Zeringue and D. J. Beebe, *Lab Chip*, 2004, 4, 91.
3. E. Leclerc, Y. Sakai and T. Fujii, *Biotechnol. Prog.*, 2004, 20, 750.
4. M. J. Powers, K. Domansky, M. R. Kaazempur-Mofrad, A. Kalezi, A. Capitano, A. Upadhyaya, P. Kurzawski, K. E. Wack, D. B. Stolz, R. Kamm and L. G. Griffith, *Biotechnol. Bioeng.*, 2002, 78, 257.
5. K. Viravaidya and M. L. Shuler, *Biotechnol. Prog.*, 2004, 20, 590.
6. Y. Kostov, P. Harms, L. Randers-Eichhorn and G. Rao, *Biotechnol. Bioeng.*, 2001, 72, 346.

7. N. Li Jeon, H. Baskaran, S. K. Dertinger, G. M. Whitesides, L. Van der Water and M. Toner, *Nat. Biotechnol.*, 2002, 20, 826.
8. T. Thorsen, S. J. Maerkl and S. R. Quake, *Science*, 2002, 298, 580.
9. H. Andersson and A. van den Berg, *Lab Chip*, 2004, 4, 98.

OTHER REFERENCES II

1. Dove, A. (2003) Nature Biotechnology 21, 859-864.
2. Entzeroth, M. (2003) Current Opinion in Pharmacology 3, 522-529.
3. Boess, F.; Kamber, M.; Romer, S.; Gasser, R.; Muller, D.; Albertini, S.; Suter, L. Toxicol Sci 2003, 73, (2), 386-402.
4. Rodriguez-Antona, C.; Donato, M. T.; Boobis, A.; Edwards, R. J.; Watts, P. S.; Castell, J. V.; Gomez-Lechon, M. J. Xenobiotica 2002, 32, (6), 505-20.
5. Cukierman, E.; Pankov, R.; Stevens, D. R.; Yamada, K. M. Science 2001, 294, (5547), 1708-12.
6. Griffith, L. G.; Swartz, M. A. Nat Rev Mol Cell Biol 2006, 7, (3), 211-24.
7. Revzin, A.; Rajagopalan, P.; Tilles, A. W.; Berthiaume, F.; Yarmush, M. L.; Toner, M. Langmuir 2004, 20, (8), 2999-3005.
8. Flaim, C. J.; Chien, S.; Bhatia, S. N. Nat Methods 2005, 2, (2), 119-25.
9. Anderson, D. G.; Levenberg, S.; Langer, R. Nat Biotechnol 2004, 22, (7), 863-6.
10. Battle, T.; Stacey, G. Cell Biol Toxicol 2001, 17, (4-5), 287-99.
11. LeCluyse, E. L.; Bullock, P. L.; Parkinson, A. Advanced Drug Delivery Reviews 1996, (22), 133-186.
12. Ben-Ze'ev, A.; Robinson, G. S.; Bucher, N. L.; Farmer, S. R. Proc Natl Acad Sci USA 1988, 85, (7), 2161-5.
13. Bhatia, S. N.; Balis, U. J.; Yarmush, M. L.; Toner, M. Faseb J 1999, 13, (14), 1883-900.
14. Berthiaume, F.; Moghe, P. V.; Toner, M.; Yarmush, M. L. Faseb J 1996, 10, (13), 1471-84.
15. Stevens, M. M.; George, J. H. Science 2005, 310, (5751), 1135-8.
16. Bissell, M. J.; Rizki, A.; Mian, I. S. Curr Opin Cell Biol 2003, 15, (6), 753-62.
17. Allen, J. W.; Bhatia, S. N. Biotechnol Bioeng 2003, 82, (3), 253-62.
18. Hung, P. J.; Lee, P. J.; Sabounchi, P.; Aghdam, N.; Lin, R.; Lee, L. P. Lab Chip 2005, 5, (1), 44-8.
19. Lee, P. J.; Hung, P. J.; Rao, V. M.; Lee, L. P. Biotechnol Bioeng 2005.
20. Puhl, G.; Schaser, K. D.; Vollmar, B.; Menger, M. D.; Settmacher, U. Transplantation 2003, 75, (6), 756-61.
21. Park, J.; Berthiaume, F.; Toner, M.; Yarmush, M. L.; Tilles, A. W. Biotechnol Bioeng 2005, 90, (5), 632-44.
22. Anderson, K.; Wilkinson, R.; Grant, M. H. Int J Artif Organs 1998, 21, (6), 360-4.
23. Landry, J.; Bernier, D.; Ouellet, C.; Goyette, R.; Marceau, N. J Cell Biol 1985, 101, (3), 914-23.
24. A. Ben-Ze'ev, G. S. Robinson, N. L. Bucher, S. R. Farmer, Proc Natl Acad Sci USA 85, 2161 (April 1988).
25. J. Landry, D. Bernier, C. Ouellet, R. Goyette, N. Marceau, J Cell Biol 101, 914 (September 1985).
26. S. A. Stoehr, H. C. Isom, Hepatology 38, 1125 (November 2003).
27. Zhang, X, Wang, W, Yu, W, Xie, Y, Zhang, X, Zhang, Y, Ma, X. Biotechnol Prog 2005, 21, 1289-96
28. Kelm, J, Timmins, N, Brown, C, Fussenegger, M, Nielsen, L. Biotechnology and Bioengineering. 2003, 83(2) 173-180.
29. Kuns-Schughart, L, Freyer, J, Hofstaedter, F, Ebner, R. J. Biomolecular Screening. 2004, 9(4) 273-285.

SUMMARY

The present invention involves methods and systems related to microfluidic structures for sample preparation, culture, and/or for performing assays or other clinical applications. Exemplary structures provided herein may be scaled to support cell cultures, cell-based assays, molecular and cellular monitoring, monitoring, culturing and assaying using nano-beads or similar structures, and drug screening processes. While a typical application of structures and methods described herein is in maintaining and/or growing cells in culture, the invention can also be adapted to handle other objects on a cellular scale, such as coated and chemically or biologically active beads, etc.

In specific embodiments, the invention involves methods and systems related to continuous cell-culture microfluidic systems. According to specific embodiments of the invention, cells are cultured with continuous fluidic mass transport of medium and optionally with humidity and temperature control.

In further specific embodiments, the invention involves a high fluidic resistance ratio microfluidic device for culturing cells inside an arrangement (or array) of microchambers, providing a tool for cost-effective and automated cell or other culture.

In certain embodiments, materials used to fabricate cell culture components are optically transparent, allowing one or more of various microscopy techniques (e.g., phase contrast, fluorescence, confocal) without disturbing the culture environment. These properties enable the realization of a portable microfluidic cell culture array that can be used in sterile or non-sterile environments for research and commercial applications.

In one example embodiment, a microchamber or a single unit of an array of culture areas consists of a roughly circular microfluidic chamber of about 40 to 50 μm in height with a high fluidic resistance fluidic passage structure, such as passages of about 1 to 4 μm in height, the fluidic passage structure providing a fluidic connection to a medium and/or reagent channel or area.

In another embodiment, the high fluidic resistance fluidic passage structure comprises one or more of an (1) undercut connection of about 1 to 4 μm, connecting to a medium channel, (2) a plurality of high fluidic resistance channels connecting between a culture area and a medium area; (3) a grid of high fluidic passages.

In another example embodiment, a microchamber or a single unit of the array consists of a microfluidic chamber of about 40 to 50 μm with a flow-around medium/reagent channel connection to diffusion micro conduits and with a single opening for receiving cells.

In further example embodiments, one or more micro culture areas are connected to a medium or reagent channel via a grid of fluidic passages (or diffusion inlets or conduits), wherein the grid comprises a plurality of intersection micro high fluidic resistance passages. In one example, passages in the grid are about 1 to 4 μm in height, 25 to 50 μm in length and 5 to 10 μm in width, the grid allowing for more even diffusion between medium or reagent channels and the culture area and allowing for easier manufacturing and more even diffusion.

According to specific embodiments of the invention, the high fluidic resistance ratio between the microchamber and the perfusion/diffusion passages or grid (e.g., ratios in the range of about 10:1, 20:1 to 30:1) offers many advantages for cell culture such as: (1) size exclusion of cells; (2) localization of cells inside a microchamber, (3) promoting a uniform fluidic environment for cell growth; (4) ability to configure arrays of microchambers or culture areas; (4) ease of fabrication, and (5) manipulation of reagents without an extensive valve network. The ability to control the cell culture environment on the microscale produces many opportunities for improving biomedical and biotechnological research.

In specific implementations, large turnover of the medium (e.g., about ~1/min) permits high cell density (e.g., >$10^7$ cells/ml) and optionally the use of $CO_2$ independent buffering of pH.

In specific embodiments, device fabrication is based on micromolding of one or more elastomers (such as, polydimethylsiloxane (PDMS)), allowing for inexpensive mass production of disposable multi-chamber or culture area arrays. Other embodiments can be constructed from bonded silicon/polysilicon surfaces or injection molded polymers.

In order to enhance control over the culture environment, the present invention in specific embodiments uses a two-level lithography process. This solves the issue of non-uniform mass transfer in microfluidic channels caused by the parabolic laminar flow profile when directly culturing cells inside the microfluidic channels. In other embodiments, a single-level lithography process is used, with the desired high fluidic resistance ratio achieved by construction diffusion passages or a diffusion grid with a small cross section, even if the passages have the same height as the culture area.

The present invention, in further embodiments, involves an integrated device or system comprising cellular handling components, one or more cell culture arrays, fluidic connections and devices, and detection and or imaging devices. In specific example systems, the intersectional design of cell culture chambers in an array provides independent cell or chamber addressing and/or allows varying of concentrations of substances in culture medium, for example to provide for a large number of different cellular environments in a very compact cell culture chamber array.

According to specific embodiments of the invention, aspects of the invention can be incorporated into one or more integrated systems that provide simple yet elegant means for advanced cell culturing in a compact space providing an ideal mechanism for high throughput screening, cells analysis, drug discovery, etc. In further specific embodiments, the novel methods and devices according to specific embodiments of the invention can be used in various systems. Applications include point of care diagnosis, tissue engineering, cell-based assays, etc.

While example systems according to specific embodiments of the present invention are described herein as used primarily for performing testing or characterizations of biological cells, it will be understood to those of skill in the art that a culture system according to specific embodiments of the present invention can be used in a variety of applications for manipulating and culturing devices at a roughly cellular size (4 μm-15 μm). These applications include, but are not limited to: cellular systems, chemical systems, viral systems, protein culturing, DNA culturing. In some such applications, known techniques for affixing substances of interest to micron or nano beads can be used to facilitate such culturing.

In further embodiments, the invention can be integrated with a complete miniaturized cell culture system for high throughput cell-based assays or other cell-based or bead based applications. A microfluidic cell culture array according to the invention offers an affordable platform for a wide range of applications in high throughput cell-based screening, bioinformatics, synthetic biology, quantitative cell biology, and systems biology.

According to further specific embodiments of the invention, a portable cell culture array can be deployed in the field or clinic for point-of-care diagnostics of infectious agents or use in personal medicine. For example, clinical cell culture is used for the detection and identification of viruses, such as the causative agent of severe acute respiratory syndrome (SARS). Doctors can also derive important information about individual patients from cultured biopsies, such as for optimization of chemotherapy regimens.

The ability to perform inexpensive high throughput experiments using methods and devices of the invention also has applications in biological research, where thorough characterizations of experimental conditions are currently limited. For example, configuration of a culture array according to specific embodiments of the invention allows the invention to be loaded and handled using systems designed for conventional 96- or 384-well microtiter plate and enables providing a different culture condition in each chamber of an array according to specific embodiments of the invention. In this example a cell culture device according to specific embodiments of the invention can assay 96 or 384 different conditions on a single chip.

In further embodiments, an array of the invention can be embodied in a fully miniaturized system in a portable assay device, for example through the integration of electro-osmotic pumps, optical sensors, and microphysiometers. A microfluidic cell culture array according to specific embodiments of the invention can be involved with a wide range of applications in high throughput cell-based screening, bioinformatics, synthetic biology, quantitative cell biology, and systems biology.

Other Features & Benefits

The invention and various specific aspects and embodiments will be better understood with reference to drawings and detailed descriptions provided in this submission. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims and equivalents.

Furthermore, it is well known in the art that systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification.

In some of the drawings and detailed descriptions below, the present invention is described in terms of the important independent embodiment of a biologic array system and components thereof. This should not be taken to limit the invention, which, using the teachings provided herein, can be applied to a number of other situations. In some of the drawings and detailed descriptions below, the present invention is described in terms of a number of specific example embodiments including specific parameters related to dimensions of structures, pressures or volumes of liquids, or electrical values. Except where so provided in the attached claims, these parameters are provided as examples and do not limit the invention to other devices or systems with different dimensions. All references, publications, patents, and patent applications cited in this submission are hereby incorporated by reference in their entirety for all purposes.

BRIEF DESCRIPTION OF THE DRAWINGS

FIG. 4A-C illustrate operation of a micro culture array device according to specific embodiments of the invention.

FIG. 5A-C illustrate operation of a micro culture array device according to specific embodiments of the invention showing long term pattern maintenance.

FIG. 10A-C illustrates a micrograph of an example high density microfluidic hepatocyte culture showing (A) time lapse (1 to 240 seconds) images of hepatocytes loaded into the microfluidic sinusoid under a driving pressure of 10 psi and (B) fluorescent viability assay on cells cultured for 7 days in the device at high cell density and (C) low cell density.

FIG. 13 illustrates as an example three out of possibly 100s of culture chambers in a system for multiplexed high cell density screening according to specific embodiments of the invention.

FIG. 14 illustrates a variation with an addition of an in-line optical or other detection region (represented with a red circle) according to specific embodiments of the invention.

FIG. 15 illustrates as an example three out of possibly 100s of culture chambers in a system useful for drug penetration/absorption screening wherein a solid mass of cells is cultured as described previously but in communication with two separated fluid flows (left and right) according to specific embodiments of the invention.

FIG. 16 illustrates as an example one out of possibly 100s of culture chambers in a system wherein a first culture region is nested inside a second culture region according to specific embodiments of the invention.

FIG. 17 illustrates as an example three out of possibly 100s of medium perfusion areas in a system useful in general purpose cell screening according to specific embodiments of the invention.

FIG. 18 illustrates as an example three out of possibly 100s of culture chambers in a system useful where multiple culture areas are arranged in parallel with a single nutrient inlet and outlet (the multiple inlet wells are connected off-chip) according to specific embodiments of the invention

FIG. 21 illustrates (a) a prototype of pneumatic manifold for an 8-unit microfluidic bioreactor chip where priming of the chip and loading cells into the microfluidic structures can be accomplished through pneumatic pumping via the pneumatic control lines as illustrated and; (b) an inverted microscope used for monitoring during the process and showing solenoid valves for controlling pneumatic pressure according to specific embodiments of the invention.

FIG. 25 (Table 1) illustrates an example of diseases, conditions, or states that can evaluated or for which drugs or other therapies can be tested according to specific embodiments of the present invention.

DESCRIPTION OF SPECIFIC EMBODIMENTS

1. Overview

Figure 1A:
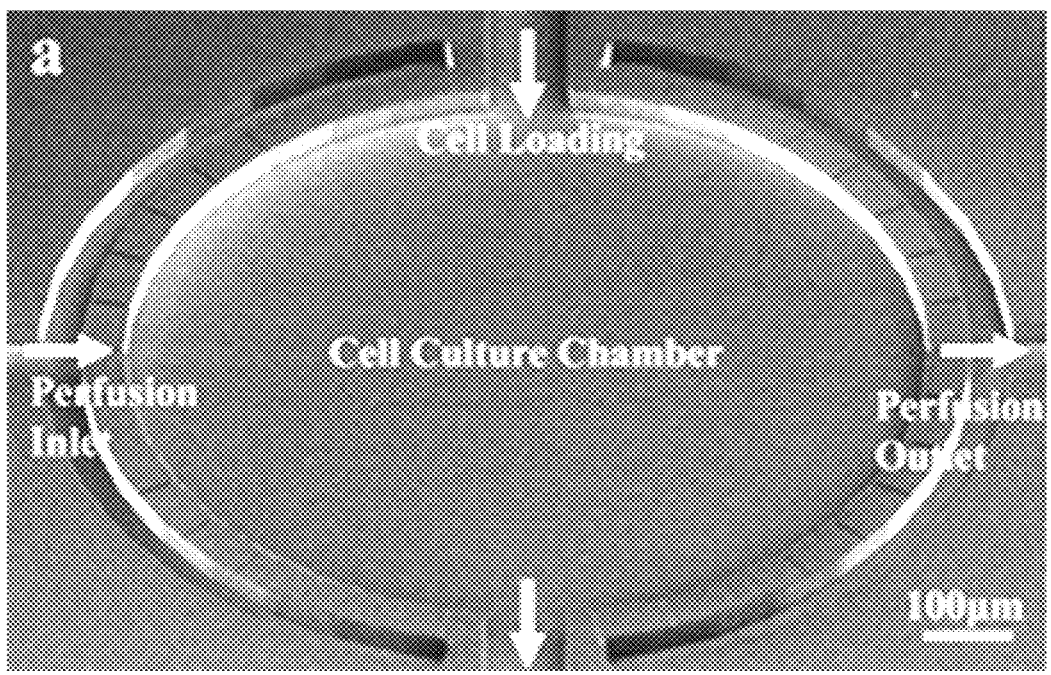
FIG. 1A is an SEM picture of a early example single unit of a device before bonding to a cover according to specific embodiments of the invention showing four external ports: (1) perfusion/medium inlet, (2) perfusion/medium outlet, (3) loading, and (4) waste outlet and showing perfusion microchannels/passages that have a substantially lower height or aspect than the other channels or the culture area.

The present invention in specific embodiments is directed to producing a miniaturized, inexpensive platform for "cell-culture-on-a-chip" to make high throughput cell experiments accessible in laboratory, clinical, and field settings. Microfabrication and microfluidic technologies are adapted and extended according to specific embodiments of the invention. Microfabricated devices according to specific embodiments of the invention can more precisely control cell culture environment than can macroscopic systems.

In one example, microfluidic structures are implemented inside a microfluidic device to provide large differences of fluidic resistances of different microchannels. The device can therefore provide uniform and controllable microenvironment for continuous medium exchange cell culture. In another example, the microstructures are controlled by pressurized microchannels for flow regulation and for cellular sample preparation. In yet another example, the high fluidic resistance (which in some embodiments may be a result of a high aspect ratio fabrication) microstructures are positioned inside or adjacent to a microchamber or micro culture area as a passive barrier for cellular and molecular sample immobilization. The device can further be integrated with electrodes for functions such as metabolism monitoring, electro-chemical product generation, electroporation, and a variety of other applications.

The design of a microscale cell culture device presents a number of unique challenges, many of which have been recently discussed. Previous demonstrations of cell culture on microfabricated devices include growth of hepatocytes, lung cells, and insect cells in both silicon and PDMS substrates. These works validated the biocompatibility, nutrient supply, and growth characteristics of cells within microfabricated devices, but have yet to realize a high throughput array that can replicate the main functionalities of traditional cell culture.

Primary cells (those removed from living humans and other animals) represent an important avenue of medical research due to their increased relevance to disease and healthy states. However, the limited availability of tissue donors and the technical difficulties of maintaining these cells in vitro have severely limited their application in biomedical research. Microfluidic systems according to various embodiments of the invention can address these technical challenges by providing an environment with microscale geometry/fluidic control that has particular advantages for maintaining cell growth and/or cell viability and also in more closely creating the environment that certain types of cells would experience in their in vivo state, in particular the densely packed or close proximity environment of living tissues and/or solid tumors or other aggregations of cells. The invention furthermore enables such systems with low sample consumption, and automated operation.

The present invention, according to various specific embodiments as described herein, provides methods, systems, and devices that address the development of a novel high fluidic resistance and/or high aspect ratio microfluidic cell culture array capable of providing a stable and uniform microenvironment for cell growth.

In specific embodiments, further elements such as heterogeneous integration of a temperature control unit such as an ITO heater, allow the invention to provide an automated cost-effective cell culture platform without the large robotic systems adapted by current practices. In specific embodiments, a microfluidic device of the invention replicates the major processes in traditional cell culture, making it adaptable to a large number of applications. As one example and for discussion purposes, 1×5 arrays are discussed for device characterization to decrease the complexity of data processing and time of optical monitoring. Other examples that are discussed herein and/or have been fabricated include a 10×10 array, a 6×6 array, an 8×8 array, and an 8×1 array.

Example Device Configurations

2. Example 1

Example Experimental Chamber

FIG. 1A illustrates a top view of an example cell culture device according to specific embodiments of the invention. This example has four ports: perfusion inlet, perfusion outlet, reagent loading, and waste, with the perfusion flow directed designated from left to right in the figure and reagent loading from top to bottom in the figure. As can be seen in the figure, the perfusion flow channels are separated from the main chamber by semi-circle-shaped perfusion channels at both the inlet (left) side and the outlet (right) side. Fluidic connection between these semi-circle-shaped channels and the culture chamber is made by the multiple high aspect ratio perfusion channels shown in the figure, which are approximately 1/10 to 1/50 the depth of the main channels and/or culture chamber. To prevent cells from flushing away during perfusion, approximately 2 µm height perfusion channels connect the perfusion inlets and outlets to the culture chamber. Because cells (typically >15 µm diameter) are inherently much larger than the perfusion channels (typically <15 µm diameter), most of the cells will stay inside the main culture chamber, which in this example is about 50 µm in height and about 1 mm in diameter. The multiple small channels used during perfusion also minimized shear flow over the cells and ensured uniform medium distribution within the chamber. Additionally, since the narrow perfusion channels create a large fluid resistance, cell and reagent loading via those channels does not require the use of microfluidic valves.

In specific embodiments, the microchambers are designed to have the same cell growth area as a typical well in a 1,536 well microtiter plate. The left and right ports are designed to provide continuous perfusion of the medium to the chamber for sustaining cell growth. The top and bottom ports are used to load cells and reagents for cell-based assays.

In a more specific example implementation, each perfusion channel is about 2 µm high and about 2 µm wide compared to the main culture chamber, which is about 1 mm in diameter and about 40 to 50 µm in height. This high aspect ratio between the chamber and the perfusion pathway into it provides numerous advantages as discussed herein.

Figure 1B:
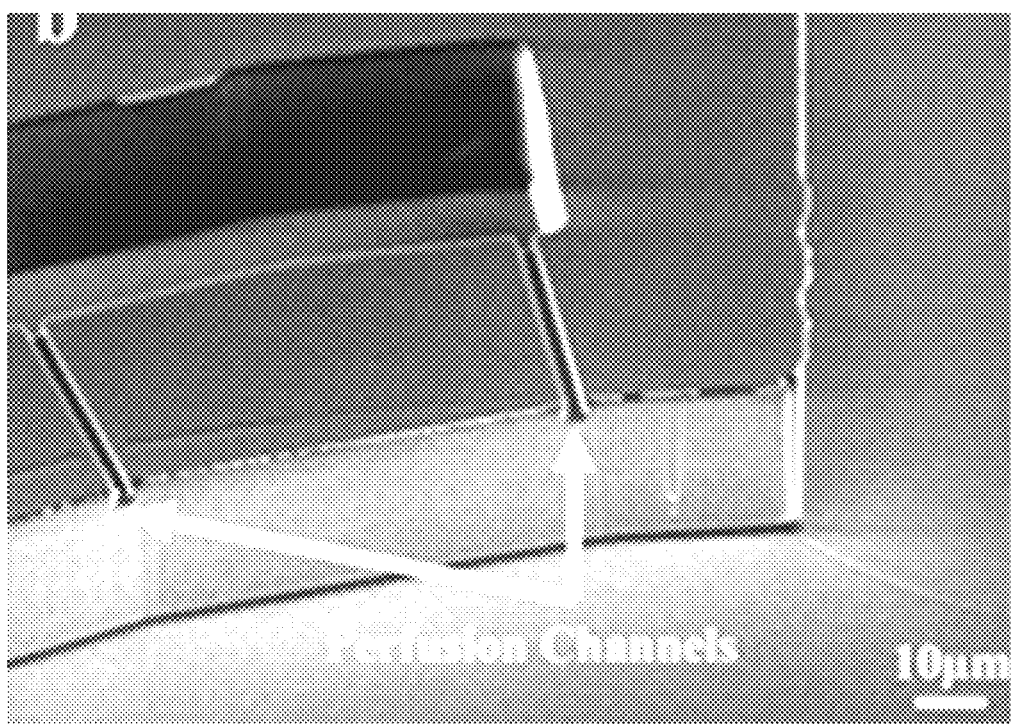
FIG. 1B illustrates an SEM image of example perfusion/diffusion channel dimensions according to specific embodiments of the invention.

FIG. 1B illustrates an SEM image of example perfusion/diffusion channel dimensions according to specific embodiments of the invention. These scanning electron microscope pictures show aspects of a single unit device before bonding, with FIG. 1B showing a closer view of the high aspect ratio design, respectively. The perfusion channels serve two main purposes. First, since they are much smaller than the size of the cells (~10 µm in diameter), they effectively prevent cells from being flushed away or from migrating outside the chamber. Secondly, the multiple perfusion channels provide uniform nutrient access inside the microchamber as will be discussed later.

It will be understood that numerous dimensional variations are possible, including chambers that are not circular, perfusion/diffusion channels that vary somewhat in dimensions between one and another, or other dimensional parameters.

Arrays

Figure 2:
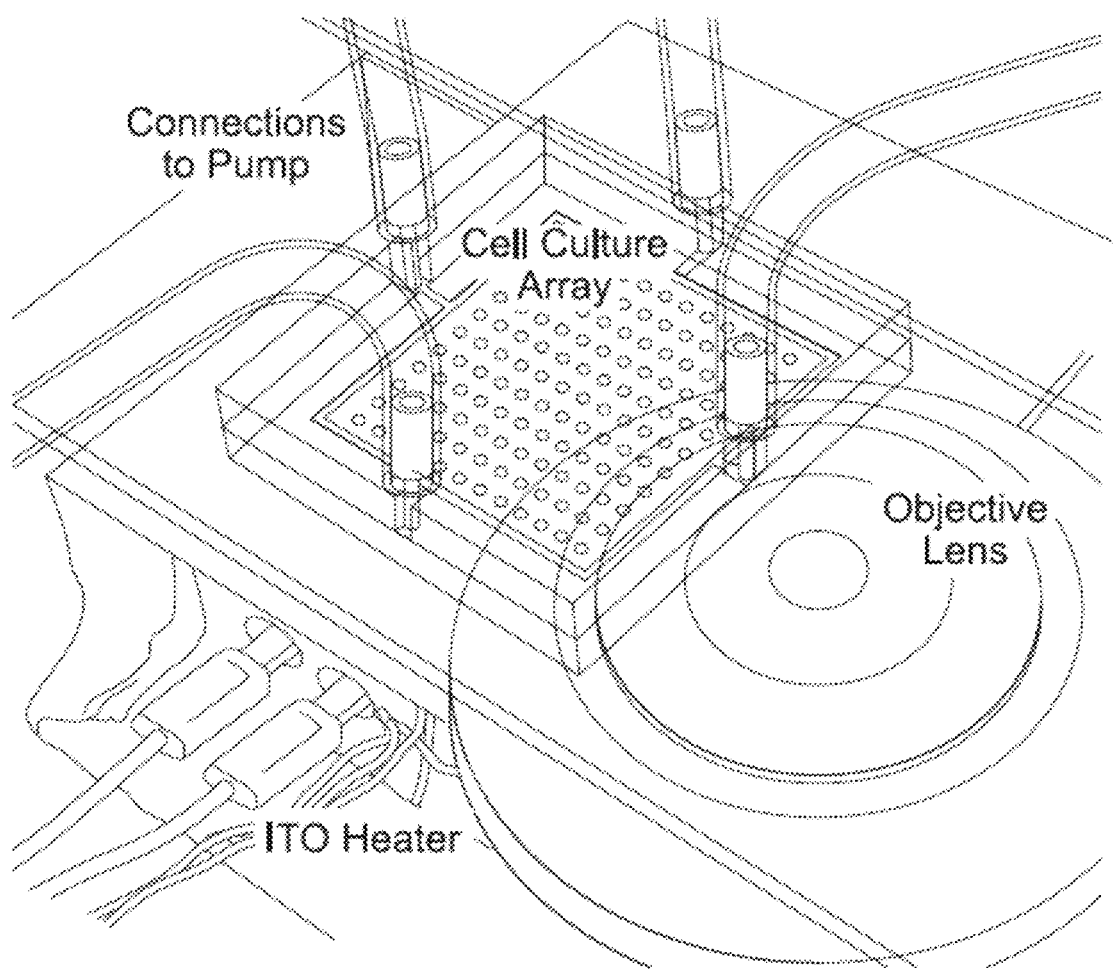
FIG. 2 is a photograph of an example 10×10 microfluidic cell culture array or system bonded to a coverglass and mounted on a transparent ITO heater and shown connected to external fluid sources and positioned above an imaging device according to specific embodiments of the invention.

In further embodiments, the invention can involve an array of culture regions, such as the examples described above. FIG. 2 is a photograph of an example 10×10 microfluidic cell culture array or system bonded to a coverglass and mounted on a transparent ITO heater and shown connected to external fluid sources and positioned above an imaging device according to specific embodiments of the invention. A microfluidic cell culture system according to specific embodiments of the invention is designed to replicate the major processes applied in standard eukaryotic culture techniques. An example device is capable of providing a closed environment for cell growth and manipulation optionally without the need of an incubator. The bonded PDMS culture chambers maintain a sterile environment while permitting gas exchange with the atmosphere. Temperature can be controlled with a transparent ITO heater without hindering monitoring of cells via optical microscopy. Humidity control of the surrounding air can be used to prevent evaporation from the microchannels, however, in specific embodiments, it has been observed that the continuous perfusion of medium is sufficient to prevent the device from drying out. Stainless steel plugs with soft tubings can be connected to the device and to a syringe pump for fluidic control. Cell growth can be using an optical microscope or other imaging device.

FIG. 2 can also include an optional microfluidic concentration gradient generator (such as discussed in Jeon et al. 2002) which is present in the left top portion of the figure and that enables multiplexing cell based assays under different conditions without increased sample preparation time. Using only two inlet concentrations, a linear gradient is generated such that each column is exposed to a different reagent concentration. Gradient generation across the columns of an example cell culture array according to these specific embodiments has been demonstrated. Initial characterization of a ten channel splitter indicated that the flow was uniform within each column, and a different reagent concentration can be introduced to different elements of the array. There was no cross flow between columns due to the high fluidic resistance imposed by the perfusion/diffusion structures. Individually addressing each column and row can furthermore be attained through the implementation of a microfluidic valve network.[15] By improving the efficiency of fluidic delivery, it is possible to introduce a level of quantitative control to experiments that are traditionally qualitative. There is also great promise in adapting microfluidic cell culture for research in tissue engineering.[16]

3. Example 2

A further example nanoliter scale fluidically addressable microfluidic platform according to specific embodiments of the invention is described below. In a specific example, an addressable 6×6 array of eight nanoliter chambers is effective for long term continuous culture of the HeLa human cancer cell line with a functional assay of 36 different cellular microenvironments. In one optional construction, high aspect ratio soft lithography is used to create the high fluidic flow channels, though further study has shown that the same high fluidic resistance can be achieved using a diffusion structures with diffusion passages that have the same height as the main chamber and medium channels. In this example, a "C" shaped ring with a narrow gap along the base is used to further separate individual culture units from flow channels to effectively decouple cell growth regions from pressure-driven transport without the use of active valves. This design avoids problems encountered in some multiplexing nanoliter culture environments by enabling uniform cell loading, maintaining long term cell localization, eliminating shear and pressure stresses on cultured cells, providing stable control of fluidic addressing, and permitting on-chip optical monitoring. The device uses a novel microstructure consisting of a high fluidic resistance roughly "C" shaped cell localization ring, and a low resistance outer flow ring. The central growth area and flow ring in one example were fabricated to be 50 µm in height, allowing cell transport through the device. The "C" shaped cell localization ring defining the 8 nl cell growth area consisted of a barrier with a 2 µm opening along the base with an inner diameter of 450 µm. This space allowed fluid flow through the cell growth area, but was narrow enough to retain cells in the central ring. An example single unit of this structure is illustrated in the SEM photograph shown in FIG. 3A.

Figure 3A:
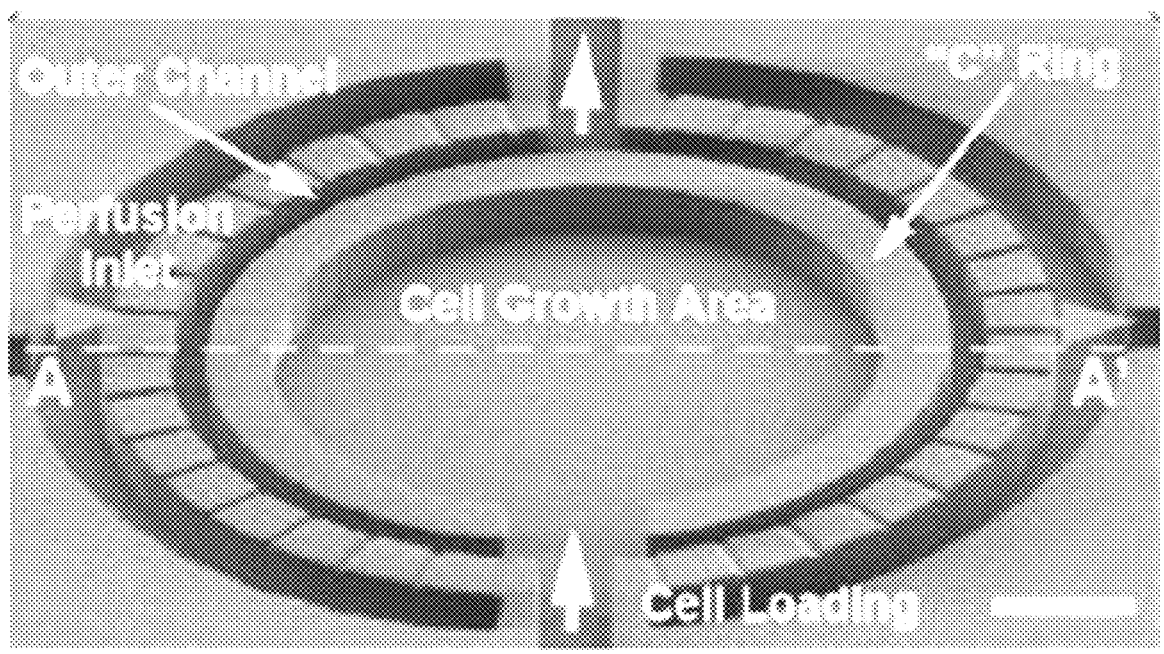
FIG. 3A-B illustrate a culture chamber array unit fabricated using soft lithography techniques from a single mold and further illustrate a chamber featuring an inner "C" barrier according to specific embodiments of the invention.
Figure 3B:
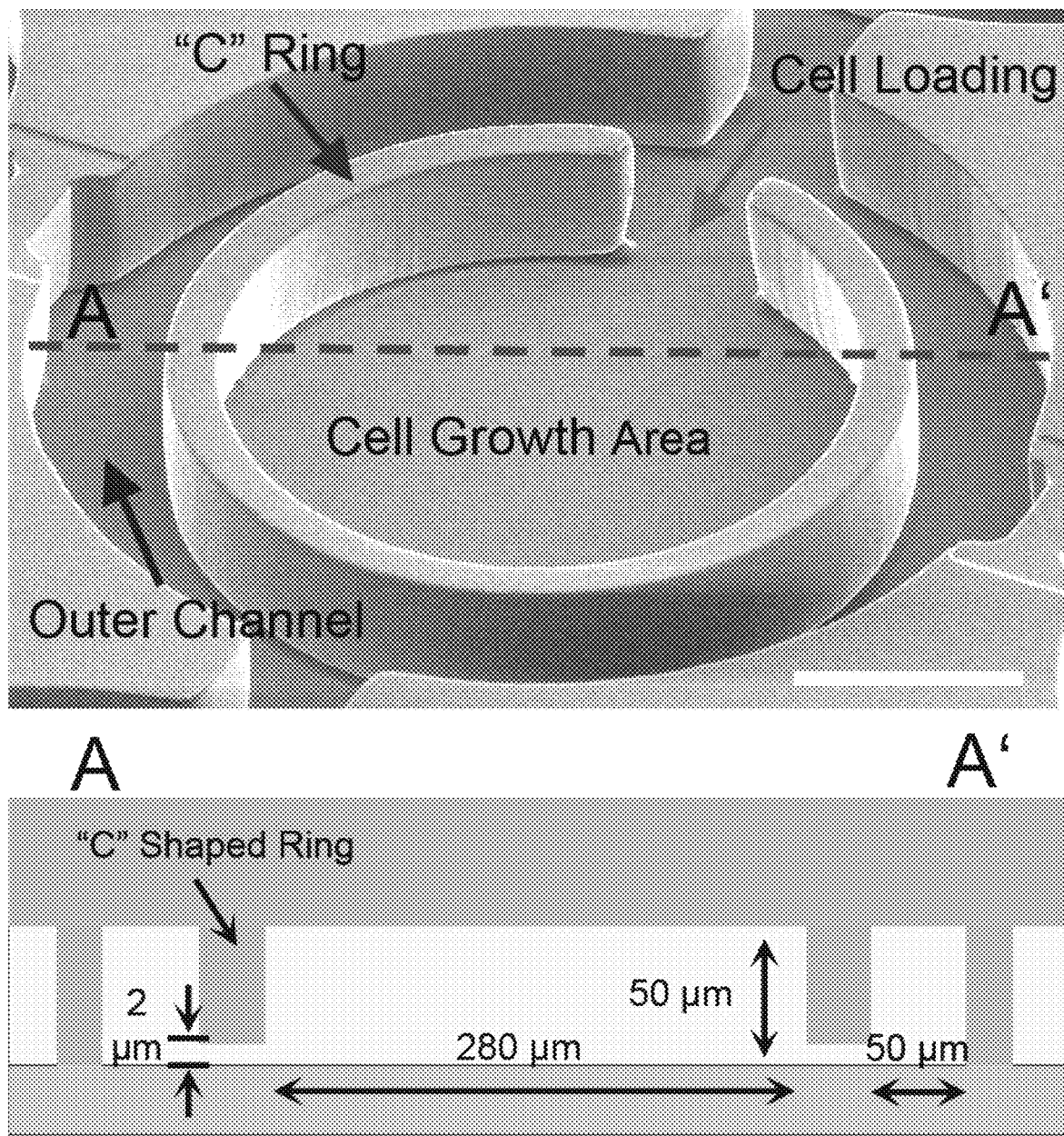

FIG. 3A-B illustrate a culture chamber array unit fabricated using soft lithography techniques from a single mold and further illustrate a chamber featuring an inner "C" barrier according to specific embodiments of the invention.

In this example, the device material consisted of PDMS elastomer covalently bonded to a tissue culture grade coverglass. FIG. 3B is an SEM image of an example single unit of an array according to specific embodiments of the invention. A central growth area was defined with a 450 µm diameter "C"-shaped localization ring with walls fabricated with a 2 µm opening along the bottom that retained cells while permitting nutrient and fluid transport (cross section A-A'). Cells were loaded into the central chamber through the opening at the mouth of the "C"-shape. The scale bar represents 100 microns. This design allows high density arrays without the need for alignment. The lower portion of FIG. 3B illustrates schematically a cross section of the device shown in the upper portion of FIG. 3B.

In these embodiments, the individual array unit consisted of a high fluidic resistance inner chamber for cell growth and a low fluidic resistance outer channel for fluid flow. The $10^3$-fold difference in resistance between the two compartments allows uniform loading of the array, controlling cell concentration, and maintaining long-term pattern integrity by selective removal of cells outside the growth area.

In an example device, these capabilities are integrated with aspects of the microfluidic cell culture array described above to produce a 6×6 addressable cell microarray for long-term functional studies. A single mold process with no required surface treatment used for fabrication allows the array to be easily scaled to a much higher size and density. In one example, a 6×6 cell analysis array with four fluidic paths to each chamber was achieved by fabricating an 8×8 matrix and sacrificing the outer row and column of culture units due to slight flow non-uniformities near the edges.

According to specific embodiments of the invention, the inlet and and/or exit of each column or row can comprise different microfluidic interface designs, for example: (1) a multiplexer (a single connection for multiple rows), (2) a concentration gradient generator, or (3) individually addressable connections. The gradient generator was a modified version of published work, and served to create multiple reagent concentrations from two fluidic inlets.

In alternative embodiments, the perfusion ring can be replaced to a high resistance passage into the outer ring, as illustrated in FIG. 3B. In further embodiments, the basic configuration as shown in FIG. 3A-B can be used for single-cell culture and trapping, which is useful in various application as will be understood in the art. In some embodiments, the cell chamber size can be reduced for optional single-cell trapping operation.

Example Operation

The 6×6 prototype is capable of culture and assay of 36 different cellular microenvironment conditions. In proof of concept experiments, human cancer cells (HeLa) were loaded into the array and cultured for 7 days to approximately $5*10^7$ cells/ml with a viability of over 97%. Row and column addressing was demonstrated by integrating a microfluidic concentration gradient generator to both dimensions, providing a different assay condition for each array unit using only 4 inlet reagents. Alternatively, individually addressing of each row can be used to allow many different reagents, drug exposure times, or time points to be assayed in this dimension.

After suspended HeLa cells were loaded into the array until the desired concentration was obtained, fresh culture medium was introduced to flush residual cells from the microfluidic channels. After loading, cells were cultured to obtain a high cell density (~300 cells/chamber). Selective maintenance was conducted every 24 hours to ensure pattern integrity. Array capabilities were demonstrated.

A finite element model was created to predict the fluid velocity profile through this structure. This analysis indicated a $10^3$-fold difference in fluid resistance between flow through the inner chamber and outer channel, agreeing with the analytical approximation based on Hagen-Poiseuille flow. This prediction was verified by tracking the flow of 2 µm beads through the microfluidic device.

Cell Loading

In this example, cell loading rate was controlled using a programmable syringe pump. For observation of cell flow through the microfluidic array, a flow rate of 40 nl/min/column was used, resulting in a flow through of approximately 0.7 cells/sec/unit. In a 100 second period, 218 cells were observed to flow through 3 separate loading columns, verifying the predicted flow rate. Cell flow velocity data within the device was obtained from analysis of time lapse digital recordings from 131 cells for the outer channel and 53 cells for the inner growth area. Uniformity of cell loading was quantified by counting cell numbers in each unit of the 6×6 array after a 2 minute loading period at 500 nl/min/column. The control condition was loaded in a 6×6 array without cell localization structures. Loading uniformity was calculated as the mean±SD (standard deviation) of the final number of cells in each row of the array, with row 1 being the closest to the inlet channel.

FIG. 4A-C illustrate operation of a micro culture array device according to specific embodiments of the invention. Due to the high fluidic resistance of flow through the 2 µm localization ring, the bulk of convective transport passed through the outer channel. This design largely decoupled the effects of pressure driven flow on cultured cells. In FIG. 4A, HeLa cell suspension was flowed through the unit at 40 nl/min to load the central rings. The cell indicated by the blue arrow was loaded into the chamber, while the cell specified by the red arrow flowed through the outer channel. In FIG. 4B, after 1 second, the difference in flow resistance was evident based on tracking the two cell velocities. In FIG. 4C, the microfluidic structure served as a cell concentrator, allowing a high density of cells to be seeded into each chamber. Since the fluidic pressure and shear stress exerted on the cells within the central ring was negligible, high cell viabilities were observed.

With a cell loading rate of 40 nl/min through each chamber, cell velocities were observed at 440±80 µm/s in the flow channel and 0.8±0.3 µm/s in the culture chamber, giving a velocity ratio of 550. This indicated that the flow rate through the central area was in the range of 50 pl/min. Under these conditions, the time scale of small molecule diffusion through the growth area (1.7 minutes) was over 4-fold faster than convective transport. The diffusion dominated mass transfer eliminated shear stresses caused by traditional continuous flow techniques while maintaining a microenvironment amenable for tissue growth. The continuous diffusion of chemicals into the culture environment may also provide a more physiologically accurate model for in vivo reaction kinetics. Additionally, the slow time scale for cellular exposure to reagents can dampen out fluctuations in assay conditions for long term studies.

The uniformity of cell loading in the 6×6 array (19% standard deviation with a minimum of 47 cells) was significantly improved compared to a microfluidic array without the loading structures under the same conditions (150% deviation with 47% of chambers empty). Initial analysis indicated that roughly 1-5% of cells entered the growth chamber. This was significantly larger than the predicted 0.2% of total flow, due largely to the tendency of cell clusters to preferentially enter the localization ring. The 2 µm opening under the cell localization ring also served as a cell concentrator by preventing trapped cells from leaving the chamber. By varying the loading flow rate and time, it was possible to completely fill the culture chambers with cells (~5*10$_7$ cells/nil). Once the cells were localized in the central growth area, they became essentially decoupled from pressure fluctuations in the attached tubing, ensuring that the cells will attach and grow in the desired regions.

Cell Culture

All microfabricated components were sterilized with UV light prior to use. Fluidic connections were sterilized with 70% ethanol and thoroughly rinsed with filtered deionized water prior to use. The device was capable of maintaining a sterile environment while being continuously handled in a non-sterile manner because all fluidic connections were sealed with epoxy, isolating the microfluidic device from the outer environment.

Cells were cultured with continuous perfusion of $CO_2$ Independent Medium (Gibco, Inc.) supplemented with 10% fetal bovine serum, 4 mM L-glutamine, and 1% penicillin/streptomycin. During perfusion, the device was placed inside a 37° C. incubator. Perfusion was controlled with a programmable syringe pump (Cole Parmer 74900), typically set at 0.4 μl/min flow through the arrayed device. Cells were cultured for over two weeks within the microfluidic array with no loss of viability.

Pattern Maintenance

As the cells began to divide within the array, it was possible to maintain the localization pattern by selectively removing cells from outside the growth area. The protease trypsin was introduced to the array to release the adherent cells from the substrate. The large flow velocity in the outer channels caused these cells to be removed from the system while cells in the growth rings were retained. Replacing culture medium to the chambers caused these cells to reattach to the substrate and resume growth. By periodically repeating this process, the cell microarray pattern could be maintained for long periods. In this experiment, the cells were purposefully allowed to overgrow the chambers to demonstrate the limits of pattern maintenance. Even when the cells had completely overgrown the outer channel, selective removal was capable of restoring the pattern such that less than 3% of cells remained outside the central ring. Scheduling treatment every 24 hours ensured over 99% of all cells remained within the central ring. More stringent control of reaction conditions and scheduling can largely eliminate residual cell debris in the outer channel. The ability to maintain cellular localization is crucial for microscale array development by preventing flow non-uniformities resulting from cell growth into the fluidic channels.

FIG. 5A-C illustrate operation of a micro culture array device according to specific embodiments of the invention showing long term pattern maintenance. In FIG. 5A, after extended culture, dividing cells began to occupy the fluidic channels. In FIG. 5B, using the trypsin protease, cells were suspended from the substrate and selectively flushed from the outer channel. Since the flow velocity was orders of magnitude lower in the central chamber, these cells were not displaced, and continued growth once medium was restored to the device. In FIG. 5C it is shown that this method ensured long term cellular localization (closed circles) compared to a control condition where no selective removal was implemented (open circles). Pattern degradation was defined as the percent of cells growing outside the central chamber.

Real-time analysis of cellular activity was readily achieved using optical interrogation. The transparency of the microfabricated device at biologically relevant wavelengths permitted seamless adaptation to fluorescent microscopy techniques used in cell biology. Single cell analysis using Raman spectroscopy on bio-functionalized nanoparticles within the cell culture microarray can also be used to monitor activity. The culture units could also be linked to downstream microfluidic analysis modules, such as one developed for single cell nucleic acid isolation and detection.

4. Example 3

Figure 6A:
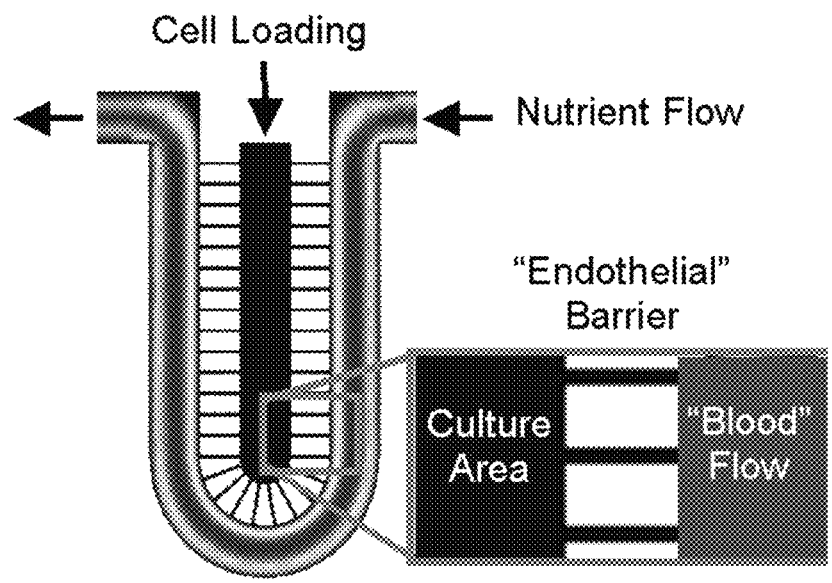
FIG. 6A illustrates a schematic view of a further example device or array element with one cell loading port and a medium or reagent channel connected thereto by a high fluidic resistance diffusion/mass transfer micro structure (eg micro inlets or passages) that have a substantially higher fluidic resistance (due to lower height and/or smaller cross-section) than the loading channel or culture area according to specific embodiments of the invention.

In a further embodiment, a culture chamber has a single opening for cell introduction and a diffusion culture medium or reagents channel that flows around the culture chamber and is connected thereto by micro inlets or micro perfusion channels. FIG. 6A illustrates a schematic view of a further example device or array element with one cell loading port and a medium or reagent channel connected thereto by a high fluidic resistance diffusion/mass transfer micro structure (eg micro inlets or passages) that have a substantially higher fluidic resistance (due to lower height and/or smaller cross-section) than the loading channel or culture area according to specific embodiments of the invention. As with other embodiments described herein, the high fluidic resistance between the passages and the microchamber allows for easy cell handling and culture. This example embodiments has particular applications for creating and/or maintaining an improved artificial tissue unit, such as an artificial liver, pancreas, kidney, thyroid, etc., for various assays and also as an improved solid tumor model.

Figure 6B:
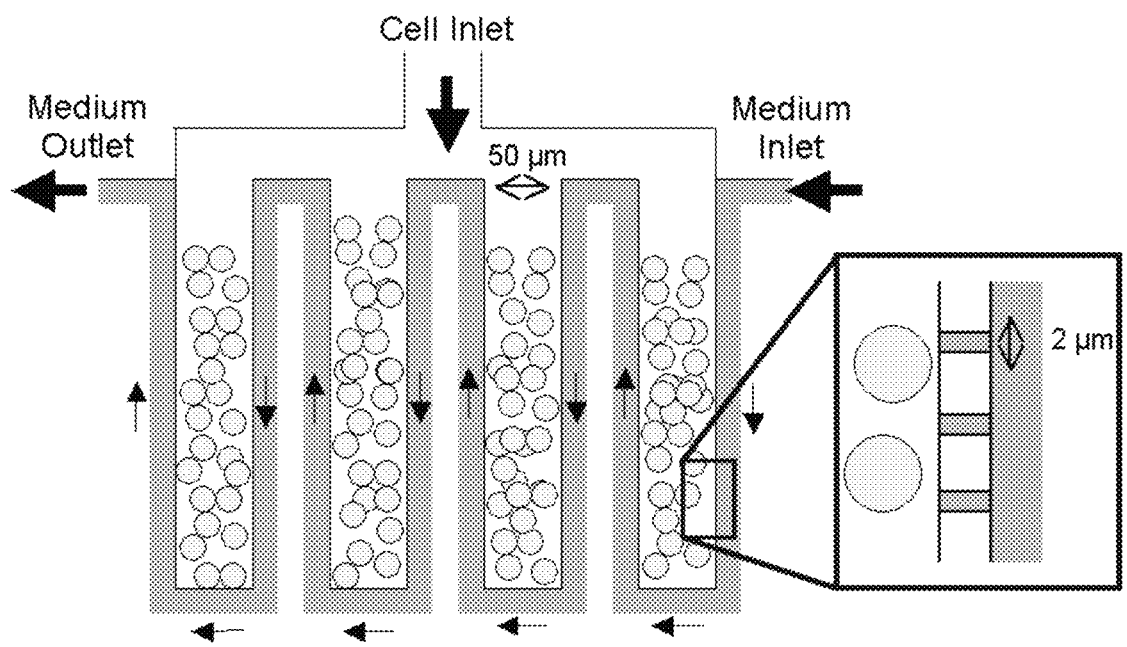
FIG. 6B is a schematic block diagram showing four culture areas each with one loading port and a medium/reagent channel flowing proximate to the culture areas and connected thereto by a high fluidic resistance diffusion/mass transfer micro structure according to specific embodiments of the invention.
Figure 7:
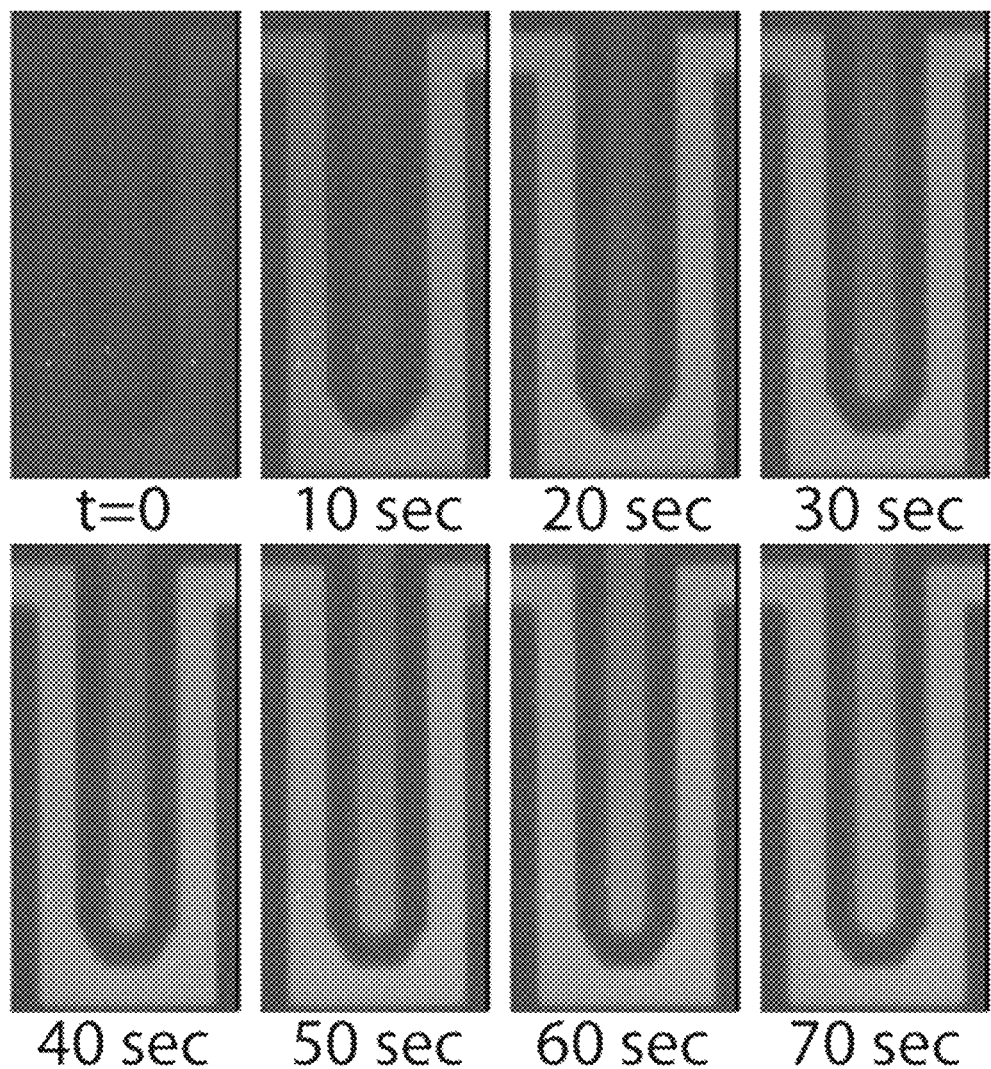
FIG. 7 illustrates liquid mass transport through the example device, showing rapid convective transport through the outer channel (indicated by the lighter colored fluid flow) with a slower diffusive transport across the high fluidic resistance micro structure (indicated by the slow diffusion of the lighter colored fluid flow into the chamber areas) according to specific embodiments of the invention.

FIG. 6B is a schematic block diagram showing four culture areas each with one loading port and a medium/reagent channel flowing proximate to the culture areas and connected thereto by a high fluidic resistance diffusion/mass transfer micro structure according to specific embodiments of the invention. This should be understood as one basic example embodiment. In alternative embodiments, the culture chambers can have different geometries, such as the "U" shaped chamber illustrated below. One aspect of this embodiment is that the medium/culture channel flows around the microchamber without being forced to flow through the microchamber as illustrated in some alternative perfusion embodiments described above. Thus, transfer of nutrients, wastes, or reagents in this embodiment is largely by diffusion. However, as discussed above, even in perfusion embodiments, some portion of the mass transfer is due to diffusion. In other embodiments, all chambers or several sets of chambers can have a shared cell loading channel as shown, but separated medium channels, allowing for a number of individual experiments to be performed on multiple duplicate cultures.

While this example embodiment has a number of applications, one of particular interest is use in facilitating an artificial liver or artificial liver sinusoid. In an example implementation, high density primary rat hepatocytes received nutrient transport via a biomimetic membrand (or vasculature or virtual membrane) according to specific embodiments of the invention. This configuration demonstrated enhanced viability and cytochrome P450 metabolic activity compared to cultures lacking this multicellular architecture.

The ability to maintain liver specific function of hepatocytes in vitro is an important area of medical and pharmaceutical research due to their central role in drug metabolism. As with most tissues, hepatocytes rapidly lose organ specific function once they are removed from the in vivo environment. While extracellular matrix coatings such as collagen I are traditionally used to maintain primary hepatocytes in culture, this is also known to down-regulate liver specific activityBy utilizing engineering capabilities with micron-scale resolution, the present invention makes it possible to recreate portions of a natural liver architecture.

In one example, a microfluidic artificial sinusoid was fabricated using soft lithography methods as described herein, and consisted of structures molded in silicone elastomer bonded to a glass culture surface. An example basic culture unit contained a 50×30×500 µm hepatic plate, a 50×30 µm cross section vessel, and a biomimetic "endothelial barrier" (or virtual membrane) separating the hepatocyte culture region from the nutrient transport vessel, wherein this biomimetic barrier or virtual membrane is constructed from one or more high fluidic resistance passages using fabrication as described herein.

The microfluidic culture unit mimics properties of liver vasculature in living tissue. Hepatocytes are prepared as a nearly solid mass of cells in "plates" about 50 µm in width. On either side of the hepatocytes are nutrient transport "sinusoids." Small cross section channels connecting the two compartments localize cells in the growth areas while allowing diffusion of medium. The flow rate (~5 nl/min), fluid velocity (~0.5-1.5 mm/sec), and cell number (~250-500) approximate values found in the liver. The high fluidic resistance ratio design between the cell seeding columns and the medium channels allow diffusion-dominant mass transfer for tissue culture. The small medium channels also prevent hepatocytes from growing into the nutrient supply channels. Thus, in particular embodiments, the present invention functionally recreates the micro-environment found in the normal human liver. In a normal liver, a "hepatocyte plate" is what physiologists typically call the aggregation of hepatocytes located between sinusoid spaces (empty regions allowing for blood flow). This configuration maximizes the number of functional cells without restricting nutrient transport. In many organs, endothelium-lined sinusoids (or spaces) provide the micro-environment for the cells that make up the tissues of an organ and tissues from these organs, as well as other tissues, are particularly suited to culturing as described herein.

Figure 8:
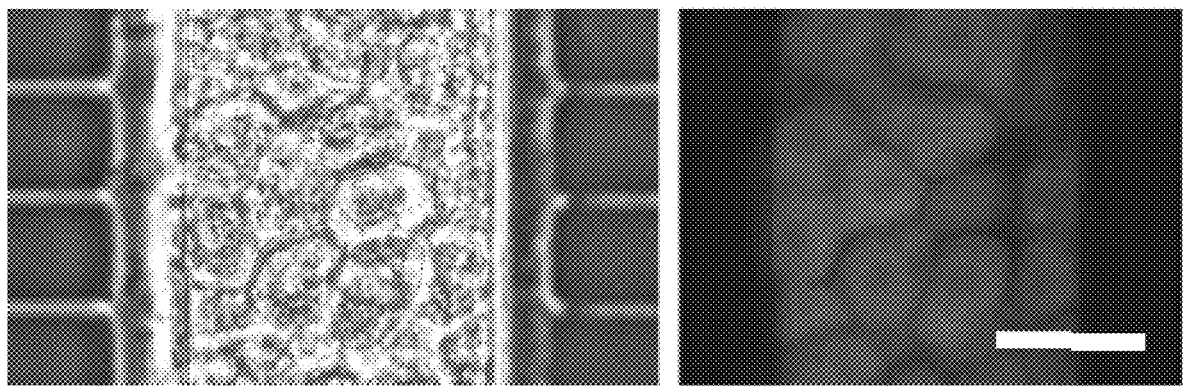
FIG. 8 illustrates a micrograph of example rat hepatocytes cultured in an example device such as in FIG. 6 wherein the fluorescence image depicts P450 metabolic activity of the same cells in a densely packed state (A) and without cell contact (B) showing that a culture chamber according to specific embodiments of the invention is able to maintain packed tissue cells in culture, allowing the cells to express more normal metabolic activity.

Returning to the example embodiment shown in FIG. 6, narrow pores within the "endothelial barrier" (e.g., about 1 to 2 µm wide by ×1 to 2 µm up to the height of the culture area tall) prevented cells from passing through, but permitted diffusive transport of wastes and nutrients. An analysis of the fluid dynamics of this microfluidic architecture indicated that the rate of nutrient diffusion into the hepatocyte culture region was roughly 100-fold greater than convective transport at the physiologically relevant blood flow rate of 10 nl/min. Furthermore, the artificial endothelium was also used as a cellular sieve to concentrate hepatocytes from suspension up to $10^4$-fold (e.g., as shown in FIG. 8 and FIG. 10) in order to create a compacted hepatocyte plate in vivo.

In order to compare the function of the artificial sinusoids according to specific embodiments of the invention to other liver cell culture techniques, isolated rat hepatocytes (Cambrex) were maintained in the suggested medium on 384-well glass bottom plates and microfluidic sinusoids at two initial cell densities. In the absence of collagen coating, hepatocytes in the microtiter plate and those lacking dense cell-cell contacts lost viability within 4 days. Plating hepatocytes at an equivalent density ($2 \times 10^5$ cells/cm$^2$) in the microtiter plate did not improve viability. An assay of liver specific P450 activity verified the increased functionality of the hepatocytes cultured in the microfluidic sinusoid (FIG. 9B). Metabolic activity was statistically equivalent from day 1 to day 7 in the microfluidic device (p>0.20). FIG. 8 illustrates a micrograph of example rat hepatocytes cultured in an example device such as in FIG. 6 wherein the fluorescence image depicts P450 metabolic activity of the same cells in a densely packed state (A) and without cell contact (B) showing that a culture chamber according to specific embodiments of the invention is able to maintain packed tissue cells in culture, allowing the cells to express more normal metabolic activity.

Figure 9A:
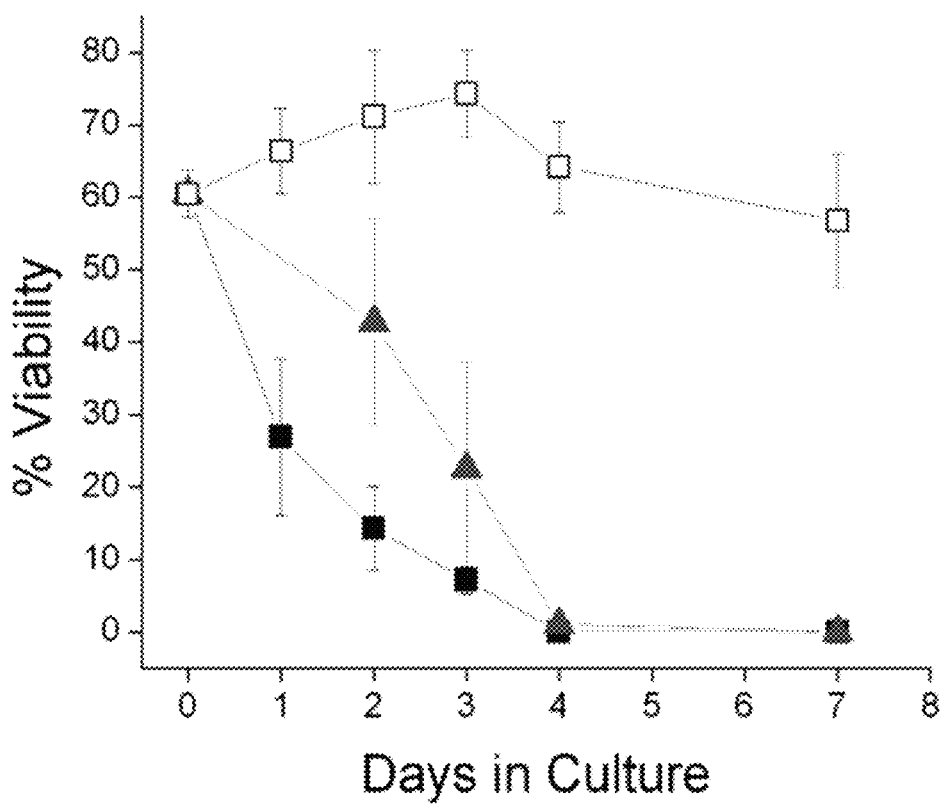
FIG. 9A is a graph indicating viability of hepatocytes cultured on a microtiter plate (■), and in an example microfluidic culture device according to specific embodiments of the invention without cell contact (1) and in a packed configuration in a microfluidic culture device (▲), where the data represent mean and SEM of 139 culture units across 15 independent chips and the graph indicates that viability of hepatocytes is greatly extended when cultured densely packed in a device of the invention.
Figure 9B:
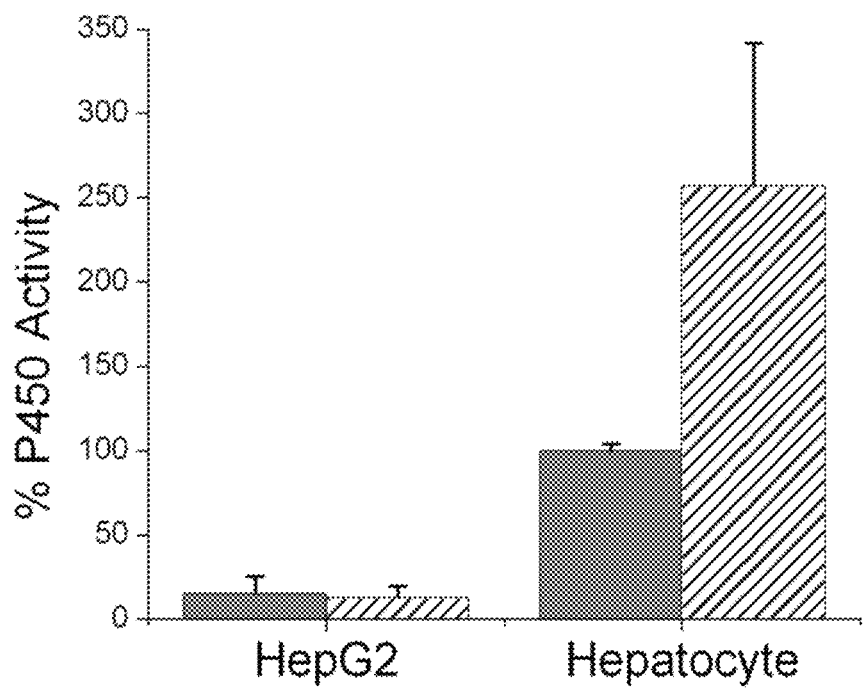
FIG. 9B shows P450 activity assayed by metabolism of 5-chloromethylfluorescein diethyl ether (10 µM, 30 minutes) in a microtiter plate (shaded) and in a microfluidic sinusoid of the invention (hatched) showing significant improvement for primary hepatocyte function ($p<0.05$) where the data represents mean and SD of fluorescence intensity of >100 cells on 3 independent chips after 5 days in culture (data normalized to microtiter plate hepatocytes).
Figure 9C:
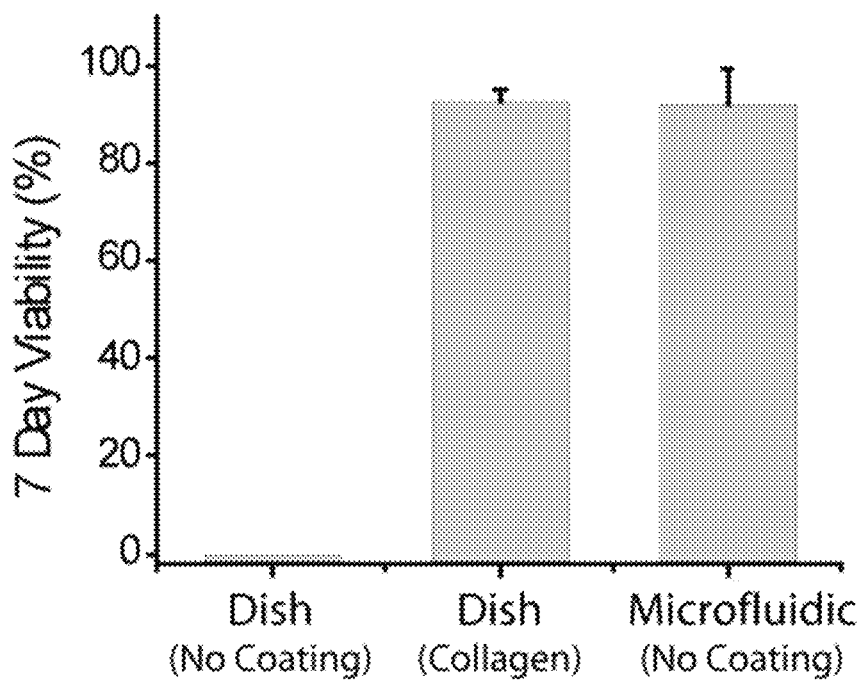
FIG. 9C compares primary rat hepatoctye viability in a device of the invention compared to a dish based culture method, indicating that in a dish-based culture a biomolecular coating (e.g. collagen) is necessary to keep cells alive, while in the microfluidic device, the unique culture chamber configuration is sufficient for cell viability over 7 days without such coating.
Figure 9D:
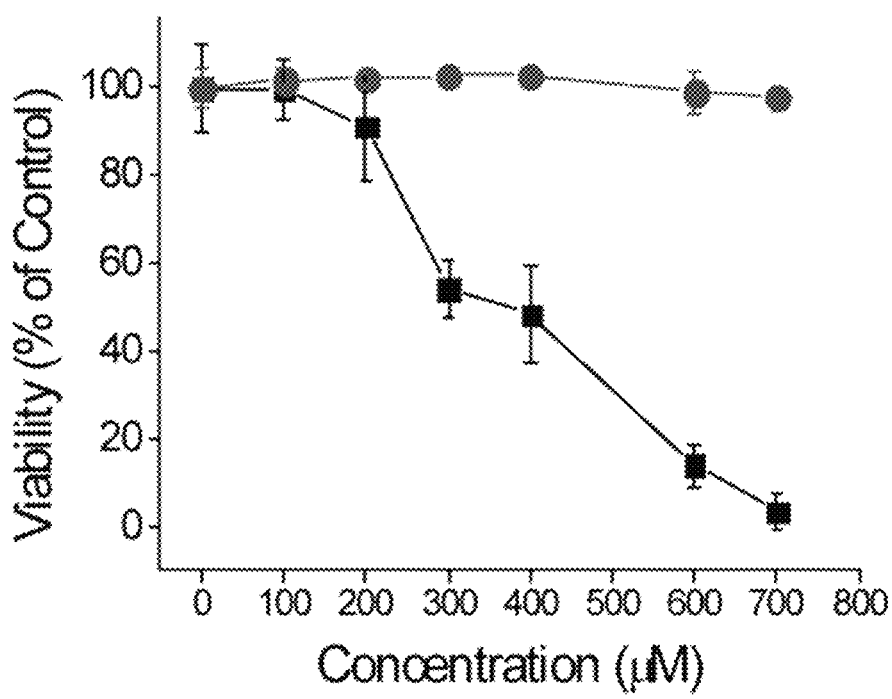
FIG. 9D is a graph illustrating primary human hepatocytes cultured in a device of the invention indicating that hepatocytes cultured according to the invention retain their liver metabolic activity.

FIG. 9A is a graph indicating viability of hepatocytes cultured on a microtiter plate (■), and in an example microfluidic culture device according to specific embodiments of the invention without cell contact (▲) and in a packed configuration in a microfluidic culture device (□), where the data represent mean and SEM of 139 culture units across 15 independent chips and the graph indicates that viability of hepatocytes is greatly extended when cultured densely packed in a device of the invention. FIG. 9B shows P450 activity assayed by metabolism of 5-chloromethylfluorescein diethyl ether (10 µM, 30 minutes) in a microtiter plate (shaded) and in a microfluidic sinusoid of the invention (hatched) showing significant improvement for primary hepatocyte function (p<0.05) where the data represents mean and SD of fluorescence intensity of >100 cells on 3 independent chips after 5 days in culture (data normalized to microtiter plate hepatocytes).

These findings indicate that the close physical contact of hepatocytes in the microfluidic sinusoid influences differentiated function. This conclusion agrees with findings on hepatocyte aggregate behavior and may be due to the importance of functional gap junctions in the intact liver (e.g., in S. A. Stoehr, H. C. Isom, *Hepatology* 38, 1125 (November 2003). Microfluidic engineering enables the control of key aspects of multicellular architecture while at the same time solving the problem of providing adequate mass transfer into tissue density cultures. The application of engineering principles described here can prove useful for the future investigation of organ function.

FIG. 10A-C illustrates a micrograph of an example high density microfluidic hepatocyte culture showing (A) time lapse (1 to 240 seconds) images of hepatocytes loaded into the microfluidic sinusoid under a driving pressure of 10 psi and (B) fluorescent viability assay on cells cultured for 7 days in the device at high cell density and (C) low cell density. The loading process is self-limiting since the resistance to flow through the sinusoid increases with cell density. Note the close cell packing attained with minimal membrane stress. In these experiments, cells were stained with Hoechst 33342 (blue), calcein AM (green), and ethidium homodimer-1 (red). Low cell density was defined as a mean center-to-center spacing of >23 µm and high density defined as <20 µm. The mean hepatocyte diameter was 20±2 µm.

5. Example 4 Grid Barrier

Figure 11A:
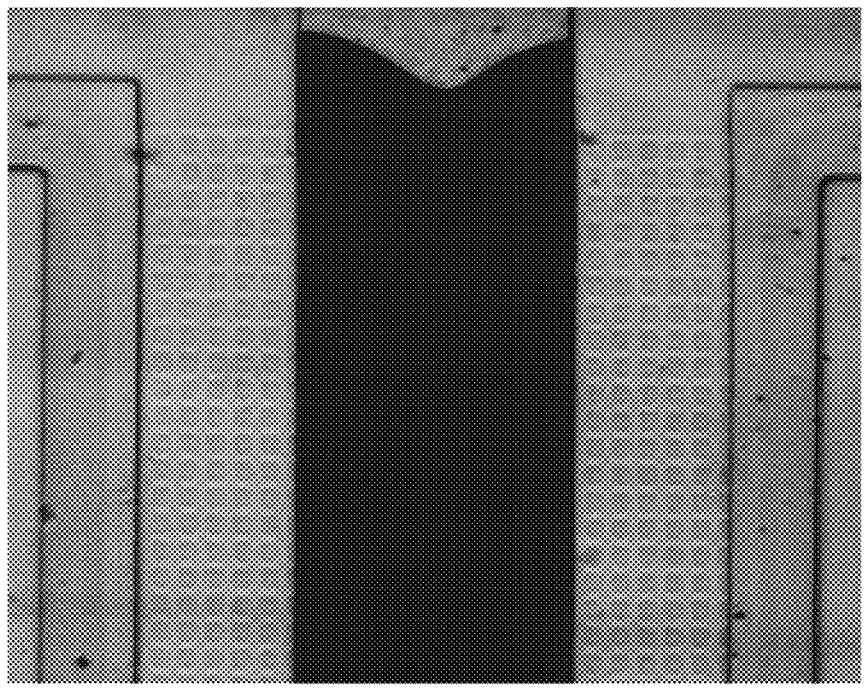
FIG. 11A is a micrograph of an example culture device with a grid-like perfusion barrier according to specific embodiments of the invention. In this example, nanoscale beads (500 nm) are shown packed into the central chamber to high density.
Figure 11B:
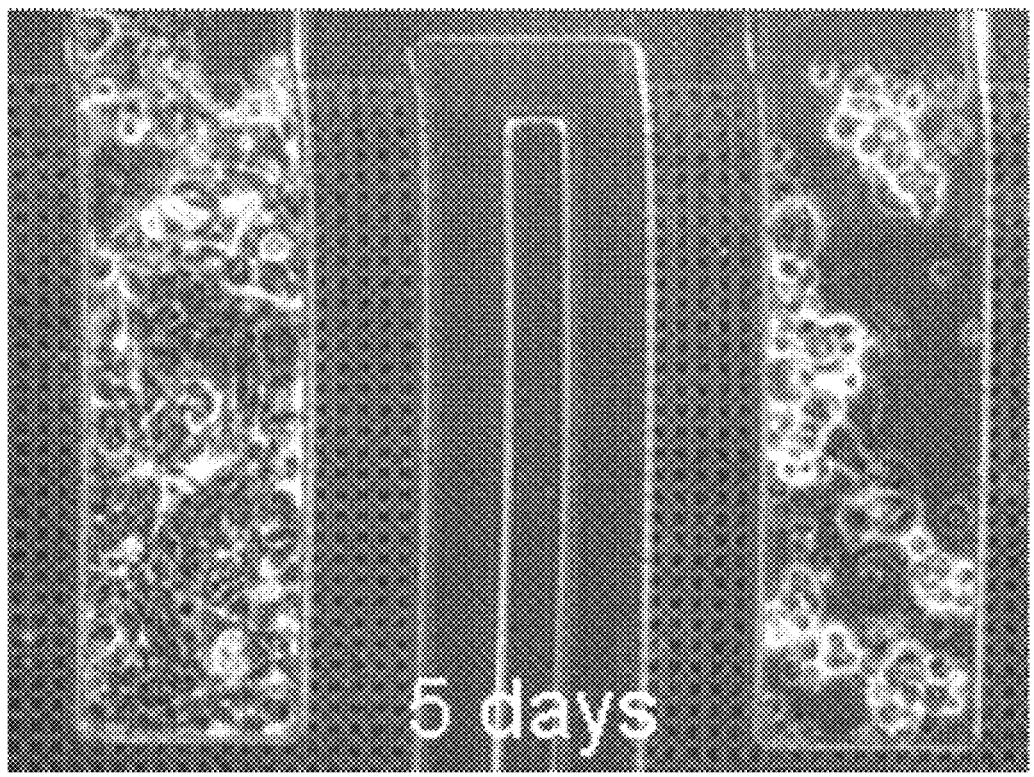
FIG. 11B is a close-up micrograph of an example of a culture device with a grid-like perfusion barrier according to specific embodiments of the invention.

An alternative embodiment to any of the devices discussed herein involves a grid-like diffusion or perfusion barrier between the medium/reagent channel and the culture area. This barrier can be constructed in a similar way to the micro inlets or passages as described above, except instead of individual inlets, a grid or other arrangement of intersecting micro inlets is used to allow perfusion fluid transport. FIG. 11A is a micrograph of an example culture device with a grid-like perfusion barrier according to specific embodiments of the invention. In this example, nanoscale beads (500 nm) are shown packed into the central chamber to high density. As with the micro passages described above, the grid passages can be much shorter than the culture area or can be near to or at the same height, according to specific embodiments of the invention.

6. Example 5

Multicellular Tumor Spheroid Model

Another application of the invention is to culture solid tumors that can perform a similar function as multicellular tumor spheroid models for cancer drug screening. Multicellular tumor spheroids (MTS) are densely packed cancer cells grown generally in suspension in culture that mimic properties of tumors inside a living organism. While MTS's are known to provide a better model for cancer drug efficacy than plate cultured tumor cells, they are limited in practice due to the difficulty of spheroid handling and difficulty in observing suspended spheroids. Using the microfluidic method described here, a much improved method to produce high density tumor-like cultures in defined structures is achieved.

Figure 12:
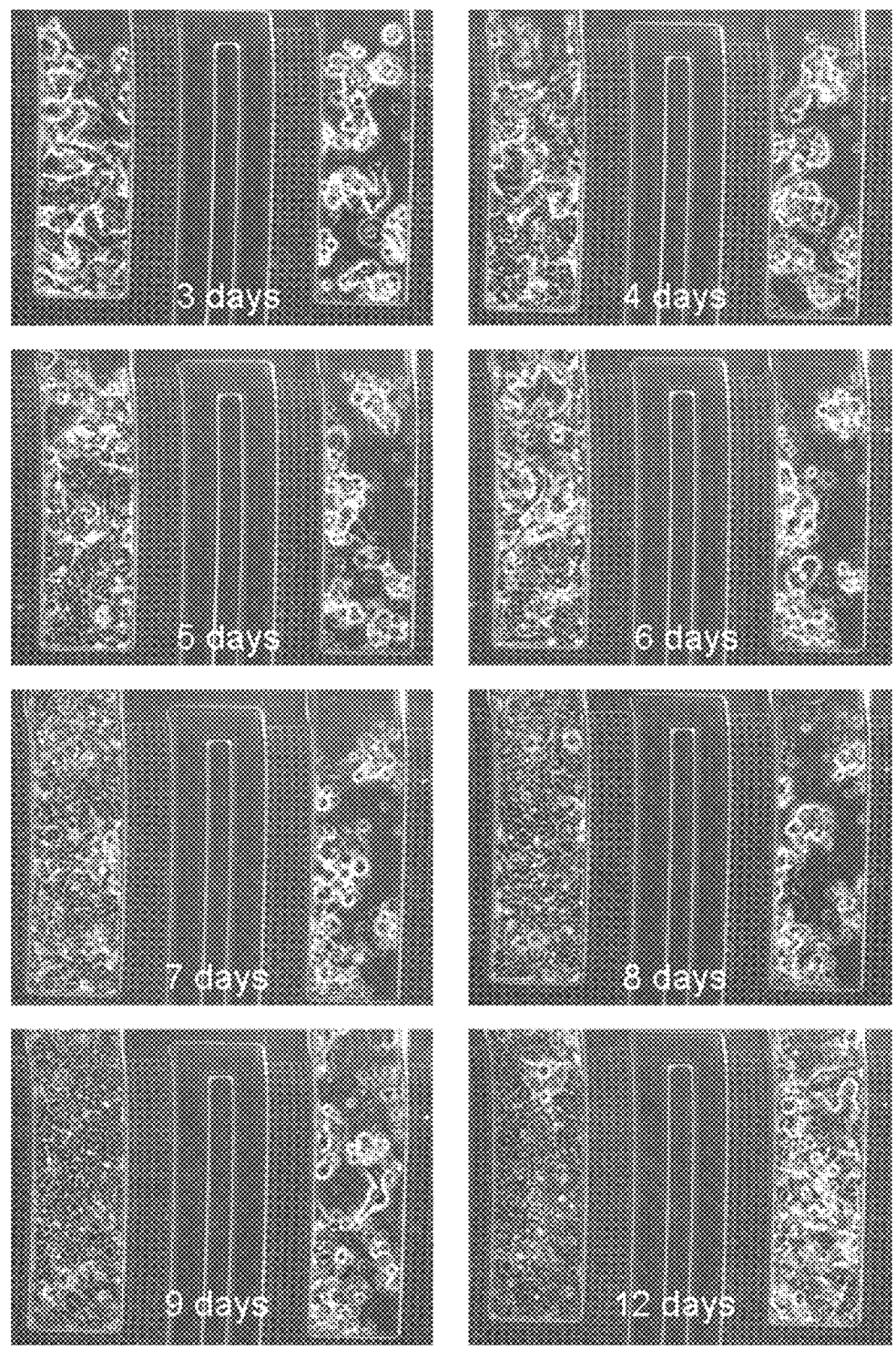
FIG. 12 is a series of micrographs illustrating an example device used to culture human cancer cells into a high density tumor-like packed configuration over a 12 day period according to specific embodiments of the invention.

Thus, according to specific embodiments of the invention, after prolonged culture of cancer cells in a microfluidic culture chamber, the cells undergo a transition in morphology and assume behavior like that found in MTS. In this condition, extensive cell-cell contacts are made that limit drug penetration into the cell mass, an extracellular matrix is produced, and individual cell boundaries become obscured. FIG. 12 is a series of micrographs illustrating an example device used to culture human cancer cells into a high density tumor-like packed configuration over a 12 day period according to specific embodiments of the invention.

7. Other Examples

FIGS. 13 thru 18 are schematic block diagrams illustrating various configurations for culture devices and/or systems according to various specific embodiments of the invention. While several diagrams primarily illustrates as the array element a squared 'U' culture chamber, it will be understood that any of the other culture chamber configurations as discussed herein could be configured as illustrated below according to some embodiments of the invention. In a number of these figures, the fluidic connections to each culture chamber are shown as separate. However, in various embodiments, these connections can be combined either on-chip or off-chip to provide larger effective culture areas or for ease of maintaining nutrient flow or collecting chamber output.

Figure 13:
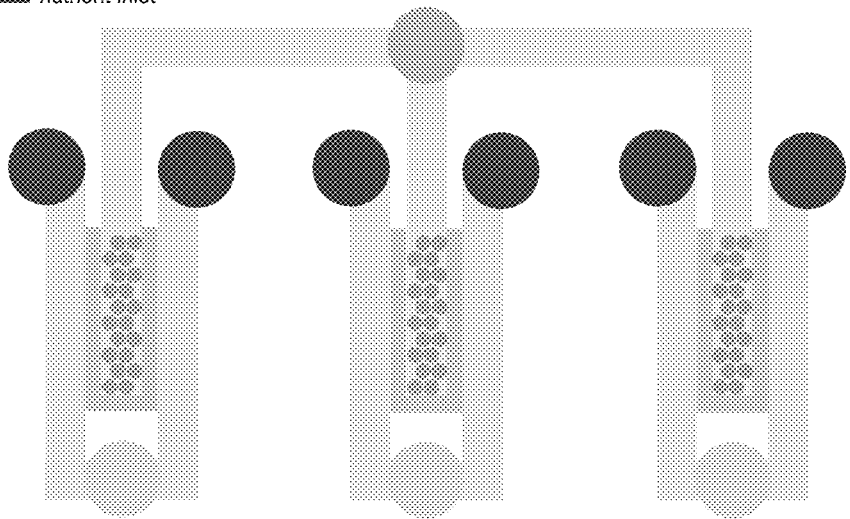
FIGS. 13 thru 18 are schematic block diagrams illustrating various configurations for culture devices and/or systems according to various specific embodiments of the invention.

FIG. 13 illustrates as an example three out of possibly 100s of culture chambers in a system for multiplexed high cell density screening according to specific embodiments of the invention. In this example, cell samples are concentrated into tissue-like regions as defined by the microfluidic barriers and maintained with a continuous flow of reagents on both sides of the cell sample. This design can be used to mimic tissues such as the liver sinusoid. This is particularly well suited for studies that involve the culture of tissue-like samples (e.g. primary cell samples). Using a single cell inlet port, multiple cell chambers can be filled, where each can then be treated with a different drug/medium combination. Cell behavior can be analyzed via microcopy methods or by collecting the flow through and performing biochemical analysis.

Figure 14:
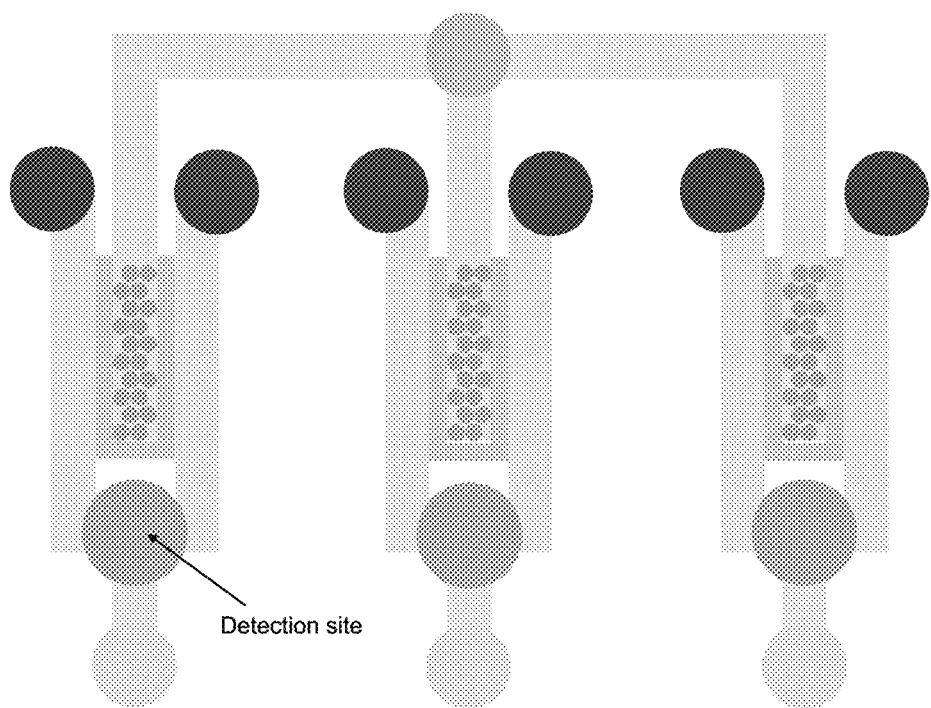

FIG. 14 illustrates a variation with an addition of an in-line optical or other detection region (represented with a red circle) For many cell based assays, endpoints are measured from the fluorescence intensity of soluble probe substrates. In this design, a microscope or spectrometer is focused on the downstream detection region to quantify cellular activity. This configuration is especially attractive for a microfluidic platform since the fluid volumes utilized are typically minimal (1-1000 nL), making traditional "bulk" measurement difficult.

Figure 15:
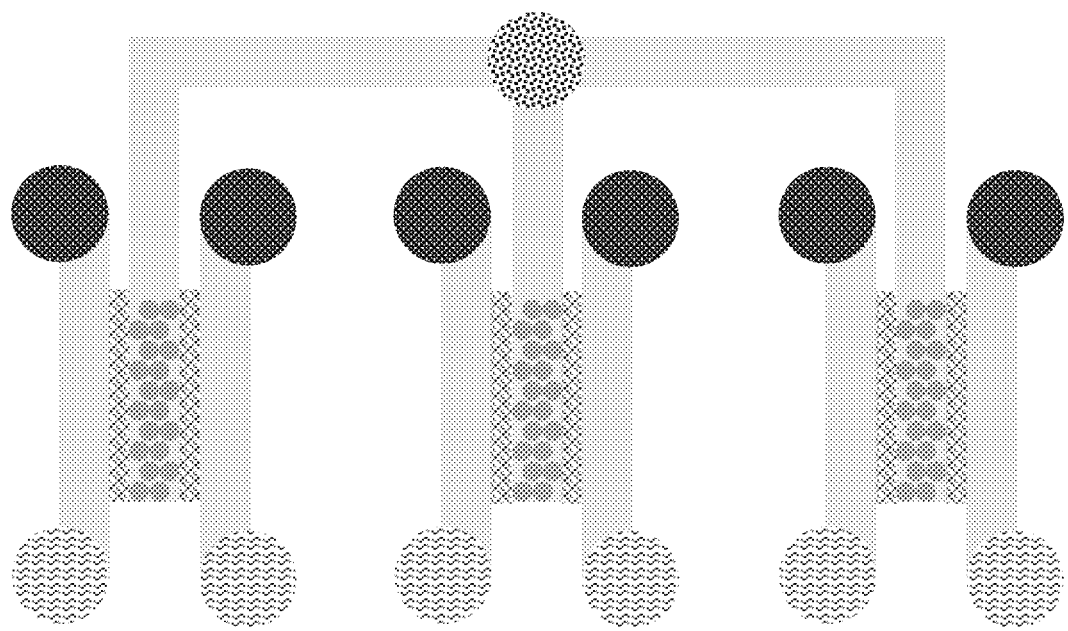

FIG. 15 illustrates as an example three out of possibly 100s of culture chambers in a system useful for drug penetration/absorption screening wherein a solid mass of cells is cultured as described previously but in communication with two separated fluid flows (left and right) according to specific embodiments of the invention. In this example, a solid mass of cells is cultured as described previously, and in communication with two sets of fluid flows (e.g., left and right). In this configuration, a chemical of interest can be introduced into one flow channel (e.g., a drug), and monitoring of the presence of the chemical or some by product or metabolite or result thereofe in the opposite channel enables the determination of drug transport kinetics and/or drug activity. This type of experiment is useful for calculating the extent of drug penetration or absorption through a tissue like culture. For example, many cancer drugs are rendered ineffective due to their inability to penetrate into the center of solid tumors. Another example is the need for pharmacologists to determine how much of a drug compound (present in the blood or digestive system) will absorb into body tissues such as blood vessels and intestinal linings. This microfluidic design uniquely enables the high throughput screening for these activities.

Figure 16:
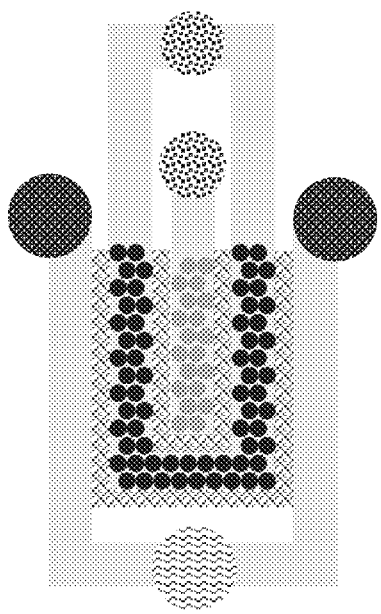

FIG. 16 illustrates as an example one out of possibly 100s of culture chambers in a system wherein a first culture region is nested inside a second culture region according to specific embodiments of the invention. In this example, one cell culture region is nested inside a second culture region. This allows the loading of two different cell types into defined locations in communication with each other. One application of this design is for the generation of an artificial multi-layer tissue such as a hepatocyte/endothelial structure. The ability to culture multiple cell types in contact with each other is known to improve physiological behaviors. In further embodiments, the fabrication techniques as described herein can be used to create structures of more than two cellular culture areas.

Figure 17:
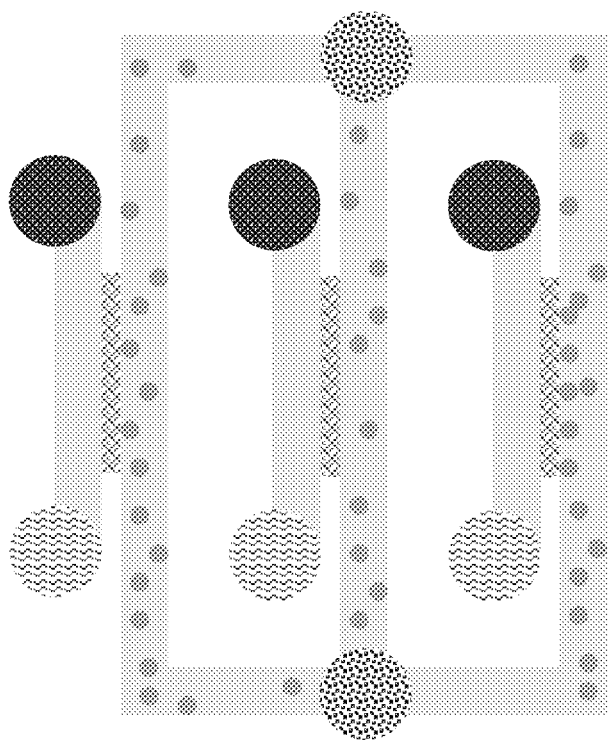

FIG. 17 illustrates as an example three out of possibly 100s of medium perfusion areas in a system useful in general purpose cell screening according to specific embodiments of the invention. This configuration may be desirable for use in general purpose cell screening. This device configuration does not concentrate the cells into a solid mass. Instead, similar to a conventional microtiter plate, the cells are distributed randomly along the culture channel. A high resistance microfluidic barrier separates the cell culture chamber from a parallel nutrient/reagent channel. This configuration replicates many of the properties of conventional macro-scale cell screening, with the advantage of a microfluidic format. One key application for this design is for performing high throughput primary cell experiments, which can be prohibitively expensive due to the large quantity of cells required per data point.

Figure 18:
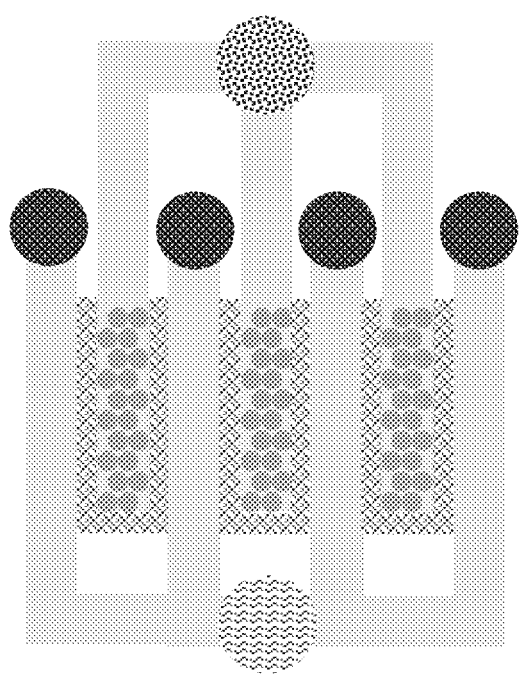

FIG. 18 illustrates as an example three out of possibly 100s of culture chambers in a system useful where multiple culture areas are arranged in parallel with a single nutrient inlet and outlet (the multiple inlet wells are connected off-chip) according to specific embodiments of the invention As one example application, this configuration mimics human liver organ tissue when hepatocytes are used. This manner of multiplexing allows many microscale units to be maintained, generating an artificial organ environment. One application of such a design would be to create an artificial liver for use in preclinical drug screening (drug metabolism and pharmacokinetics). Another potential application is for construction of an artificial organ to produce a compound or substance of interest or to perform a biologic or therapeutic function. In this example design, each well on the bioreactor is SBS standard size (3.5 mm in diameter) and the cell seeding columns are positioned in the center of the drug inlet and perfusate outlet wells; therefore, the bioreactor is compatible with standard plate readers.

Primary Cell Applications

In addition to the described experiments, a chamber array according to the invention is suited for use with all currently utilized primary cell samples. Primary cells are those harvested from living animal tissue, and are particularly useful for tests where physiological responses are important (e.g. drug screening). Companies such as Cambrex and AllCells are specialized in preparing and selling primary cell samples. Due to the limited supply of primary cell samples, they are not easily integrated into large scale screens. The advantage of a controlled microfluidic format is that with the same number of cells, the throughput of experiments can be increased by 100×. Additionally, since it is important to maintain primary cell function in culture, a microfluidic system enables better control of culture conditions.

A special category of primary cells are stem cells. These cells are capable of differentiation into various cell phenotypes under different conditions. For example, the human embryonic stem cell is known to be able to differentiate into every cell type found in the adult human body. Stem cell culture currently is practiced by maintaining high density colonies of stem cells in well controlled environments. Therefore, the invention described here is ideally suited for applications in stem cell culture, maintenance, and controlled differentiation.

System Example

Figure 20:
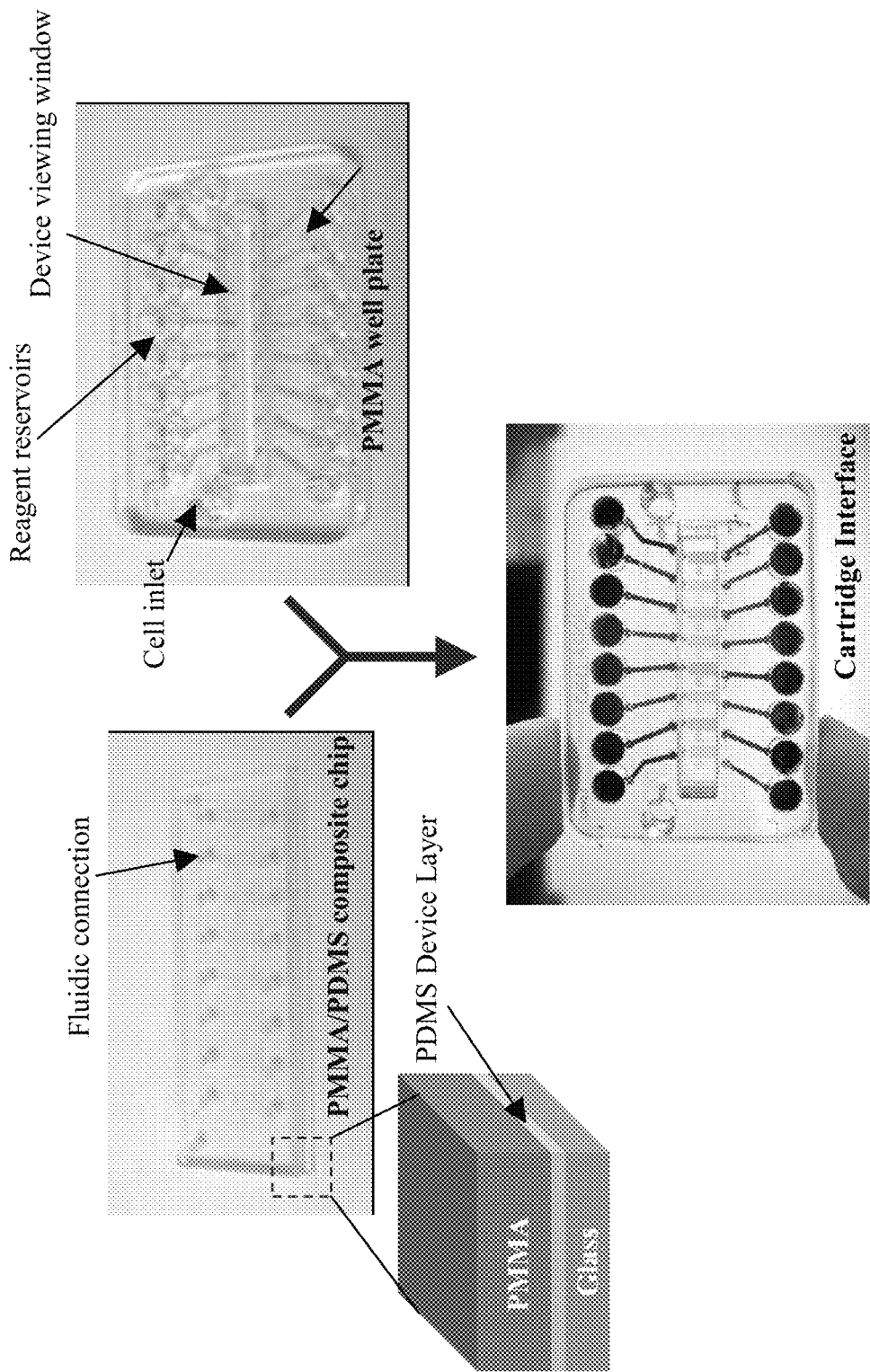
FIG. 20 shows the fabrication results of an 8-unit microfluidic bioreactor chip according to specific embodiments of the invention.
Figure 22A:
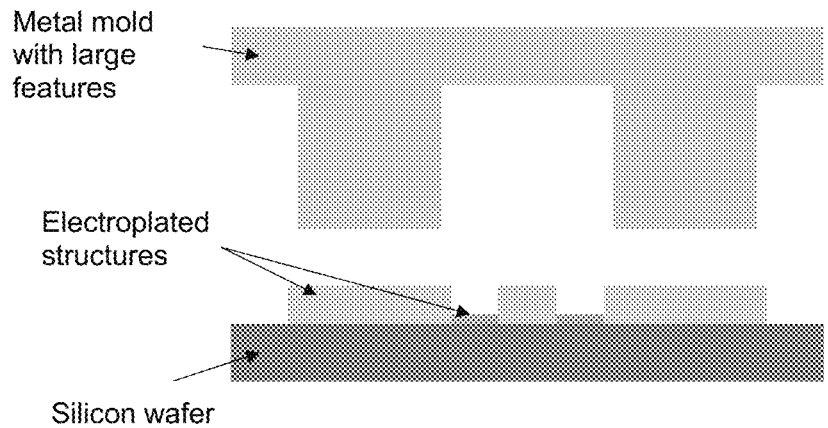
FIG. 22A through FIG. 22F illustrate a fabrication flow for an all plastic microfluidic plate using injection molding and adhesive bonding technology.
Figure 22B:
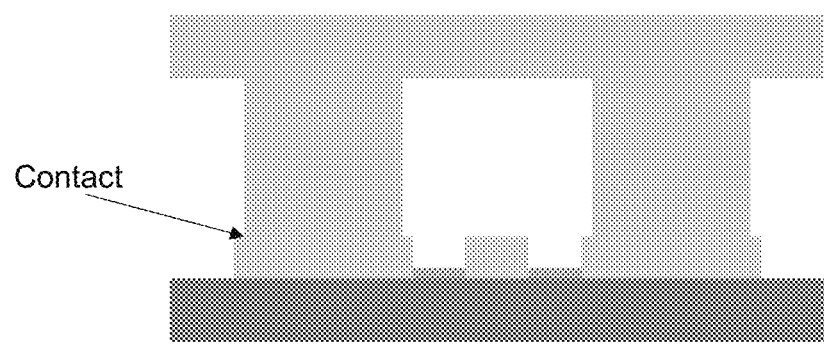
Figure 22C:
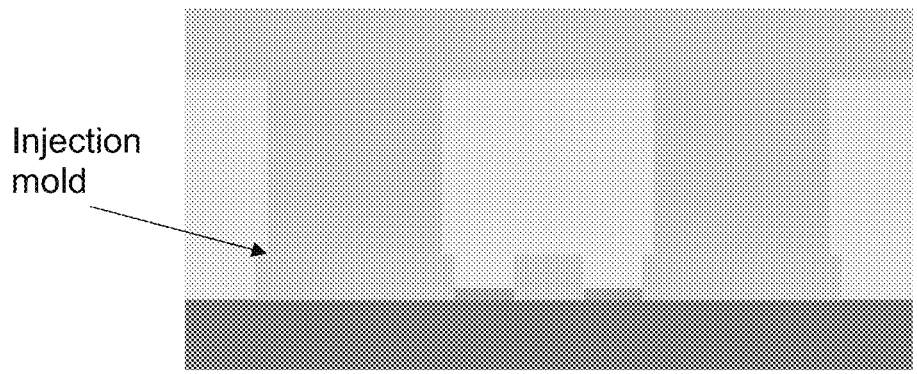
Figure 22D:
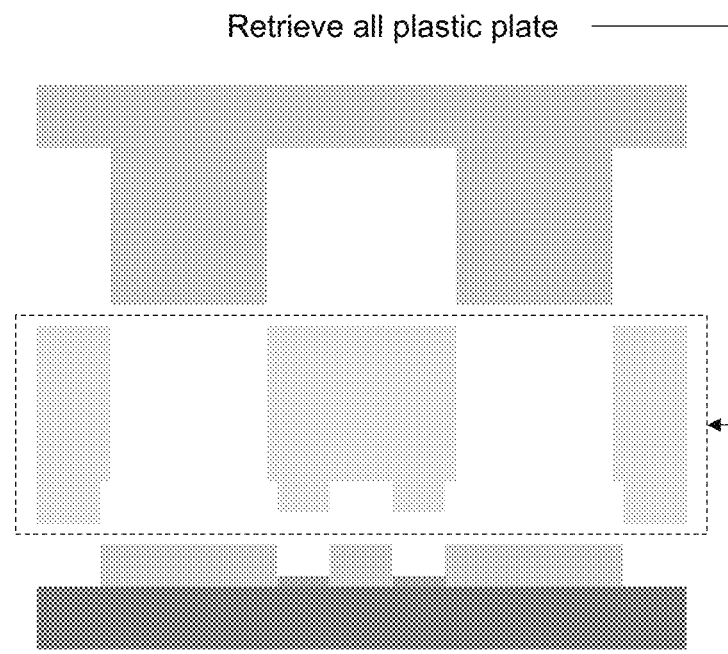
Figure 22E:
Figure 22F:
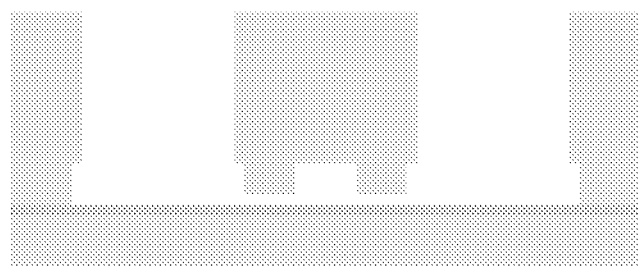

In one example embodiment, operation of the artificial liver microfluidic device is accomplished using an interface platform with each example chip containing 8 independent cell culture experiments, with a separate inlet and outlet reservoir. FIG. 20 shows the fabrication results of an 8-unit microfluidic bioreactor chip according to specific embodiments of the invention. A novel fabrication process was developed to sandwich PDMS microfluidic structures between PMMA and glass. The PMMA/PDMS composite chip was then bonded to a PMMA well plate using acrylic adhesives. The operation of the bioreactor chip was verified by confirming food dyes flowing from the top reservoirs to the bottom reservoirs through the PDMS microfluidic structures. In this example, the culture microchambers and microfluidic connections are located on a central area, interfaced to an SBS standard well format (e.g., a standard size for 384 well plates). In the figure, blue and red dyes are shown at alternating inlet reservoirs at one side of the chip, with the outlet reservoirs at the other side of the chip. This example configuration allows eight independent cell culture experiments, with each of the eight separate regions in the central portion having one or more sinusoid microchambers as described herein. At right in the figure is pictured an optional manifold used for flow control in this example. However, gravity flow can also be utilized as described herein. The chip is inserted into the manifold, which provides precise pneumatic pressure control for medium/reagent flow. The transparent chip and manifold is depicted on a microscope stage, where cell behavior can be readily monitored.

Thus, this embodiment provides independent addressable medium/reagent channels that are not connected. For example, in one configuration as shown in FIG. 20, each inlet port/reservoir connects to exactly one outlet, allowing, for example, testing of 8 different chemicals by placing 8 separate liquids into the 8 inlet ports. While in this example, each of the 8 units shares the same cell loading inlet, due to the high resistance barrier in each unit, there is functionally no communication between the 8 "independent" inlet/outlet flows.

In an example operation, cell loading is performed on all eight chambers simultaneously, allowing significant cell savings. The poly-dimethyl-siloxane (PDMS) based microfluidic device is interfaced with a standardized "well plate" format (acrylic), allowing direct pipeting of culture medium and reagents. The fabrication of the chip enables visualization of all fluidic flows using standard microscopy or high content screening methods. For cell loading and initial priming, a custom built air pressure control manifold is used. Due to the low flow rates necessary for medium perfusion (~5 nl/min), a simple gravity driven flow method by tilting the plate to make inlet wells higher than the outlet wells in conjunction with fluidic resistance patterning method can be used to achieve reliable operation in some embodiments, though other pumping mechanisms can also be used.

The microscale nature of the culture device enables research to be performed with significant cell/reagent savings. In current operation, it takes only 5,000 cells (5 μl at $10^6$ cells/ml) to completely fill the 8 unit device. Currently, cell loading is accomplished in under 5 minutes with over 90% of the cells localized to the growth regions. Further optimization is expected to increase the loading efficiency to nearly 100% (all cells placed in the well end up in the microfluidic growth region) by standardizing the cell loading conditions (cell density, loading medium, flow rate) to minimize cell loss in the upstream fluidics. In preliminary observations, a medium flow rate of 5 nl/min (~8 μl/day) was sufficient to maintain HepG2 cells. Therefore, the standard 384 microtiter well size inlet and outlet reservoirs (containing 100 μl) are sufficient to maintain long term culture (with occasional replenishment). Flow rate through the device during culture is maintained using gravity driven hydrostatic pressure. This is achieved by placing the chip on a fixed incline. By carefully designing the fluidic resistance in the microfluidic channels and the incline angle, initial observations show that a 7.4±1.1 nl/min can be sustained over long periods. The tolerance of this flow (15%) is expected to be much better (<2%) by improving the quality and uniformity of fabrication.

Cell culture within the array was verified using the HepG2 human hepatoma cell line. These observations indicate that there is no nutrient limitation even for very high density cultures after 7 days of gravity driven flow. Furthermore, the viability remained nearly 100% in all 8 units on the chip, and across 3 independent chips, indicating that there are no fundamental flaws in the design or operation.

Preliminary observations of primary rat hepatocyte (Cambrex Bioscience) culture in the device indicated a similar altered morphology that is not observed in plastic dish culture (FIG. 8). Presumably, the cell-cell contact enabled by the microfluidic device signals the formation of "liver-like" aggregates, similar to those observed in ECM and spheroid culture. Preliminary data indicates that this culture configuration greatly enhanced cell viability (FIG. 9). Even in the absence of surface coating, cell-cell contact seemed capable of maintaining high hepatocyte viability in the microfluidic format.

FIG. 21 illustrates (a) a prototype of pneumatic manifold for an 8-unit microfluidic bioreactor chip where priming of the chip and loading cells into the microfluidic structures can be accomplished through pneumatic pumping via the pneumatic control lines as illustrated and; (b) an inverted microscope used for monitoring during the process and showing solenoid valves for controlling pneumatic pressure according to specific embodiments of the invention. As described herein, in specific embodiments a novel fabrication process was developed to sandwich PDMS microfluidic structures between PMMA and glass. The PMMA/PDMS composite chip was then bonded to a PMMA well plate using acrylic adhesives. The operation of the bioreactor chip was verified by confirming food dyes flowing from the top reservoirs to the bottom reservoirs through the PDMS microfluidic structures. In an example setup, after chips were loaded, they were put into a $CO_2$ incubator (Ferma Scientific) for environment control. An inclined design gravity flow rack is used for large scale perfusion experiments. The flow rate resolution is at nanoliters.

8. Example Fabrication Methods

Systems and devices as described herein can be fabricated using any techniques or methods familiar from the field of photolithography, nano-fabrication, or micro-fluidic fabrication. For completeness of this disclosure and to discuss additional and independent novel aspects according to specific embodiments of the invention, specifics of example fabrication methods are provided below.

In some embodiments, the microdevices are fabricated using a single mold process, allowing direct array scale-up as well as the capability of integration with additional microfluidic layers. The development of a microfluidic high throughput automated cell-based assay platform allows rapidly determining or observing multiple cellular parameters for applications in quantitative cell biology and systems biology.

In alternative specific embodiments, a high density, scalable microfluidic cell array is implemented using a novel design to mechanically decouple cellular compartments from fluid flow. This is accomplished again using a method of high aspect ratio soft lithography technology, which consists of patterning two different channel heights and/or two different channel widths on a single mold such that fluidic resistance can be finely controlled over up to five orders of magnitude. By localizing cell growth to predefined areas, fluid transport through the array is carefully controlled and isolated from cellular activity.

FIG. 22A through FIG. 22F illustrate a fabrication flow for an all plastic microfluidic plate using injection molding and adhesive bonding technology.

Figure 23:
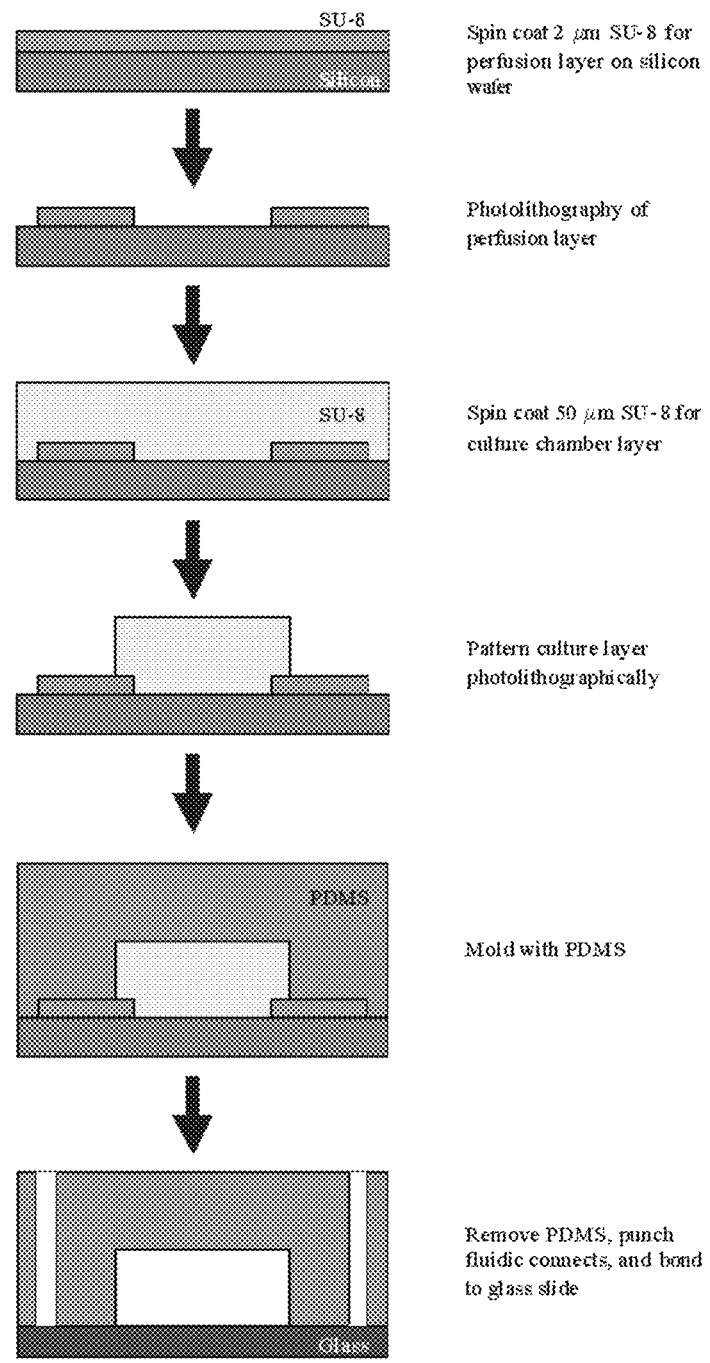
FIG. 23 illustrates a schematic fabrication process diagram for an example fabrication according to alternative specific embodiments of the invention.

FIG. 23 illustrates a schematic fabrication process diagram for an example fabrication according to alternative specific embodiments of the invention. An example microfluidic cell culture array according to specific embodiments of the invention was fabricated by using soft-lithography technology and replicate molding. This process consisted of patterning a polymer mold on a silicon wafer followed by replication with a soft elastomer. SU-8 negative photoresist (Microchem Corportion) was used as the mold material. First, the SU-8 2002 was patterned on a silicon wafer to define a high fluidic resistance structure (e.g., 2 µm high channels and/or a gap under or over a C- or other structure between the outer channel and culture chamber. A 40 to 50 µm SU-8 2050 layer was then spin coated on top of the perfusion channels. Because the SU-8 2050 is substantially thicker than SU-8 2002, the surface was planarized after spin coating. The cell culture chamber and other channels were then photolithographically defined. PDMS (Sylgard 184, Dow Corning Corporation) was prepared with a 10:1 ratio between the base and the curing agents. The PDMS was then poured on the 2-level SU8 mold. The mold was degassed in a vacuum chamber for 10 min before curing in a 70° C. oven for 4 h.

The device dies were then cut by a razor blade and the fluidic connection ports were punched using an 18 gauge flat tip needle. The device was then irreversibly bonded to a coverglass (Fisher Scientific) after oxygen plasma treatment (PlasmaTherm Etcher, 50 W, 2 Torr, 40 s) on both the bottom of the device and the glass slide. 20 gauge stainless steel connectors (Instech Laboratories) and soft tubings (Cole Parmer Corporation) were used to provide fluidic connections to a syringe pump (Cole Parmer 74900).

In alternative embodiments, (e.g., for the artificial tissue microfluidic device) a different fabrication method was used. An example 8-unit microfluidic bioreactor chip was manufactured by heterogeneously integrating PMMA reservoirs with PDMS microfluidic devices. The previous described method demonstrate the use of PDMS and soft lithography technology for a syringe pump driven cell culture array. For higher throughput cell-based experimentation, an alternative fabrication method was used to "sandwich" PDMS between a PMMA sheet and a glass slide to facilitate integration with plastic-based materials. In this particular example, the PDMS is 0.5 mm thick, the PMMA sheet is 1.5 mm thick and the glass slide is 1mm thick. The composite PMMA/PDMS microfluidic chip was then bonded to another piece of PMMA plate containing reagent reservoirs and fluidic connections. FIG. 20 shows the fabrication results of the 8-unit microfluidic bioreactor chip. The PDMS microfluidic features were fabricated using the conventional soft lithography technology as described above and the PMMA well plate was cut by a 25 W VersaLASER $CO_2$ laser cutter. Transparent acrylic cement was then applied to adhesively bond the PMMA/PDMS composite chip to the PMMA well plate.

9. Example Operation

Operation of the microfluidic bioreactor chip was accomplished using an interface platform developed at CellASIC. Each bioreactor chip currently provides 8 independent culture experiments, each with a separate inlet and outlet reservoir, and according to specific embodiments of the invention cell loading can be performed on all eight chambers simultaneously, significantly saving the biomasses. The standard PMMA well plate format allowed direct pipetting of cells, culture medium and reagents. The fabrication of the chip also enables visualization of all fluidic flows using standard microscopy or high content screening methods. For cell loading and initial priming, a custom built air pressure control manifold is used. Due to the low flow rates necessary for medium perfusion (~5 nl/min), a simple gravity driven flow method proves to be reliable. In addition, each bioreactor chip can be primed and loaded with cells separately, and then put into an incubator for gravity-driven perfusion on inclined racks.

Example all Plastic Fabrication

Figure 19:
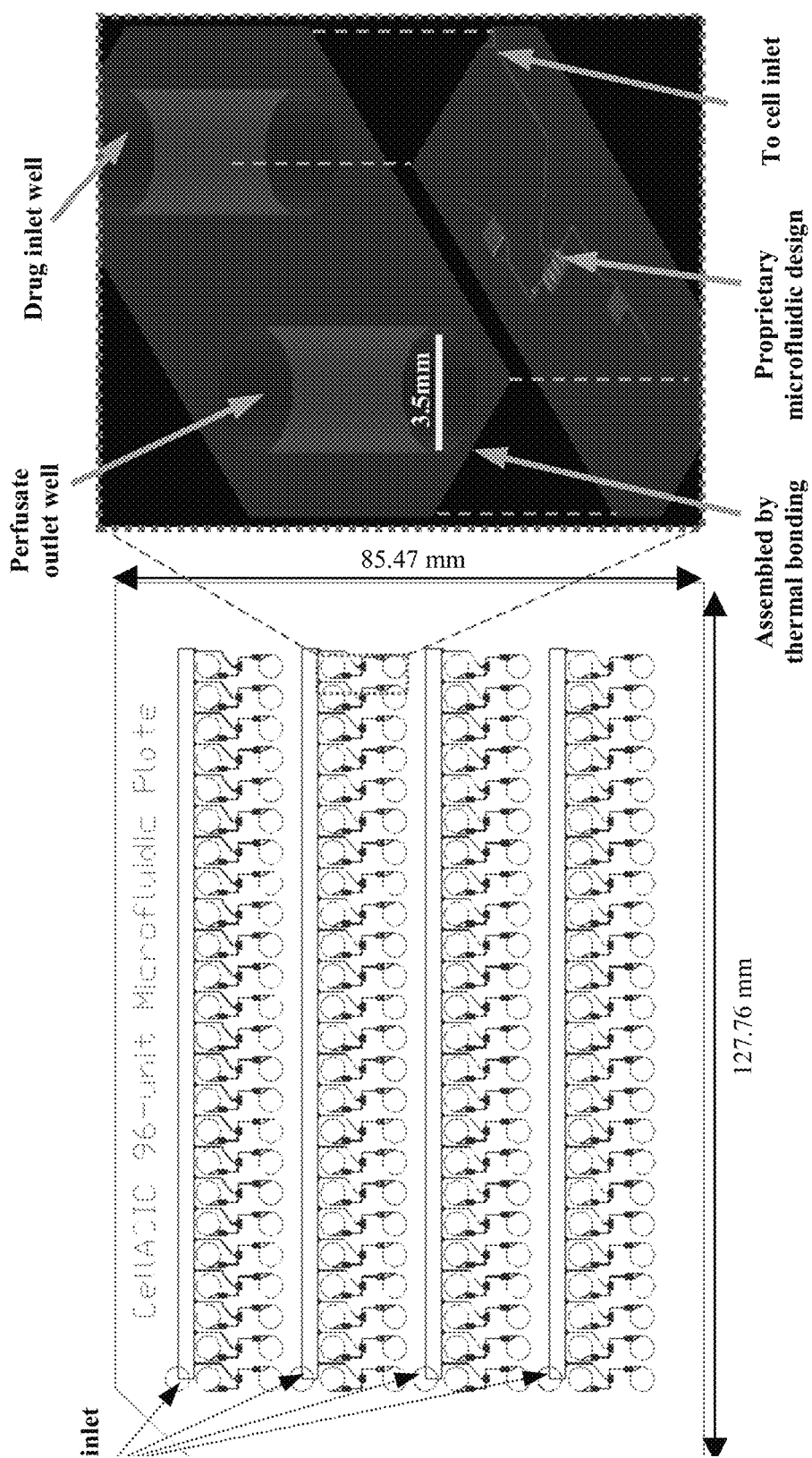
FIG. 19 illustrates a CAD drawing of a proposed 96-unit PMMA microfluidic bioreactor wherein in this example each well on the bioreactor is SBS standard size (3.5 mm in diameter) and the cell seeding columns are positioned in the center of the drug inlet and perfusate outlet wells; therefore, the bioreactor is compatible with standard plate readers.

In further embodiments, a culture device can also be fabricated with all plastics. FIG. 19 illustrates a CAD drawing of a proposed 96-unit PMMA microfluidic bioreactor wherein in this example each well on the bioreactor is SBS standard size (3.5 mm in diameter) and the cell seeding columns are positioned in the center of the drug inlet and perfusate outlet wells; therefore, the bioreactor is compatible with standard plate readers. In this example, 96 continuous medium cell-based experiments can be conducted on a single acrylic plate. Since the bioreactor plate is SBS standard, it is compatible with the existing robotic liquid handling system and plate reader; therefore, the plate itself can be a modular integration in existing research labs. To facilitate high throughput data acquisition, the fluidically trapped cells are positioned in the middle of the drug inlet and the perfusate outlet wells; therefore, the luminescent or fluorescent signals from the cells can be directly read from a conventional plate reader for cell-based assays.

Figure 24:
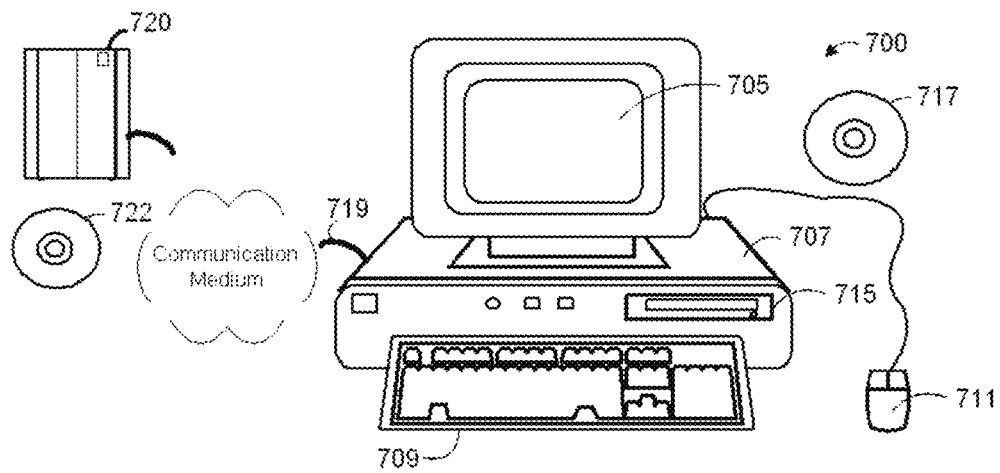
FIG. 24 is a block diagram showing a representative example logic device in which various aspects of the present invention may be embodied.

To fabricate the microfluidic bioreactor plate, a 6 mm thick PMMA sheet (McMaster-Carr) is laser cut (25 W $CO_2$ laser, VersaLASER) or injection molded to create a top piece containing all cell inlets, drug inlets and perfusate outlet wells. A hard polymer master template (or silicon master template or electroform master template) such as those that can be fabricated in Berkeley Microfabrication Laboratory, is then hot embossed (Tetrahedron Associates, SPF-8) into a 1.5 mm thick PMMA sheet (McMaster-Carr) to create a bottom piece with microfluidic structures. Other than hot embossing, injection molding can also be an option. The top and bottom pieces are then thermally bonded together (Tetrahedron Associates, SPF-8) to complete the microfluidic plate. It is also possible to have the microfluidic structures, inlet and outlet wells on a same single piece. FIG. 24 depicts the overall fabrication steps.

Various groups have successfully demonstrated hot embossing of nano- to micro-sized features using different master templates, as well as thermal bonding between two PMMA sheets; however, CellASIC is the first one to apply these processes for high throughput cell-based experimentations. The key parameters to address are temperature, pressure and time. The major challenge is the deformation of PMMA during the bonding process. Because the minimum features in various designs according to specific embodiments of the invention, are at micron-scale, the control of temperature in some example fabrication methods is critical. An alternative approach is to use adhesive bonding by spin coating an adhesive layer at a thickness thinner than any microfluidic device features on the plate to prevent blockage of microfluidic channels.

10. Diagnostic and Drug Development Uses

As described above, following identification and validation of a assay for a particular cellular process, in specific embodiments devices and/or systems as described herein are used in clinical or research settings, such as to screen possible active compounds, predicatively categorize subjects into disease-relevant classes, text toxicity of substances, etc. Devices according to the methods the invention can be utilized for a variety of purposes by researchers, physicians, healthcare workers, hospitals, laboratories, patients, companies and other institutions. For example, the devices can be applied to: diagnose disease; assess severity of disease; predict future occurrence of disease; predict future complications of disease; determine disease prognosis; evaluate the patient's risk; assess response to current drug therapy; assess response to current non-pharmacologic therapy; determine the most appropriate medication or treatment for the patient; and determine most appropriate additional diagnostic testing for the patient, among other clinically and epidemiologically relevant applications. Essentially any disease, condition, or status for which a biologic culture is useful can be evaluated.

Web Site Embodiment

The methods of this invention can be implemented in a localized or distributed data environment. For example, in one embodiment featuring a localized computing environment, a microchamber culture device according to specific embodiments of the present invention is configured linked to a computational device equipped with user input and output features. In a distributed environment, the methods can be implemented on a single computer, a computer with multiple processes or, alternatively, on multiple computers.

Kits

A device according to specific embodiments of the present invention is optionally provided to a user as a kit. Typically, a kit of the invention contains one or more microchamber culture array devices constructed according to the methods described herein. Most often, the kit contains a diagnostic sensor packaged in a suitable container. The kit typically further comprises, one or more additional reagents, e.g., substrates, tubes and/or other accessories, reagents for collecting blood samples, buffers, e.g., erythrocyte lysis buffer, leukocyte lysis buffer, hybridization chambers, cover slips, etc., as well as a software package, e.g., including the statistical methods of the invention, e.g., as described above, and a password and/or account number for accessing the compiled database. The kit optionally further comprises an instruction set or user manual detailing preferred methods of using the kit components for sensing a substance of interest.

When used according to the instructions, the kit enables the user to identify disease specific cellular processes. The kit can also allow the user to access a central database server that receives and provides expression information to the user. Such information facilitates the discovery of additional diagnostic characteristics by the user. Additionally, or alternatively, the kit allows the user, e.g., a health care practitioner, clinical laboratory, or researcher, to determine the probability that an individual belongs to a clinically relevant class of subjects (diagnostic or otherwise). In HTS, a kit according to specific embodiments of the invention can allow a drug developer or clinician to determine cellular responses to one or more treatments or reagents, for diagnostic or therapeutic purposes.

Embodiment in a Programmed Information Appliance

The invention may be embodied in whole or in part as a logic or other description for construction of the devices according to specific embodiments of the invention, In such a case, the invention may be embodied in a computer understandable descriptor language, which may be used to create fabricated devices that operate as herein described.

Integrated Systems

Integrated systems for the collection and analysis of cellular and other data as well as for the compilation, storage and access of the databases of the invention, typically include a digital computer with software including an instruction set for sequence searching and/or analysis, and, optionally, one or more of high-throughput sample control software, image analysis software, collected data interpretation software, a robotic control armature for transferring solutions from a source to a destination (such as a detection device) operably linked to the digital computer, an input device (e.g., a computer keyboard) for entering subject data to the digital computer, or to control analysis operations or high throughput sample transfer by the robotic control armature. Optionally, the integrated system further comprises valves, concentration gradients, fluidic multiplexors and/or other microfluidic structures for interfacing to a microchamber as described.

Readily available computational hardware resources using standard operating systems can be employed and modified according to the teachings provided herein, e.g., a PC (Intel x86 or Pentium chip-compatible DOS,™ OS2,™ WINIDOWS,™ WINDOWS NT,™ WINDOWS95,™ WINDOWS98,™ LINUX, or even Macintosh, Sun or PCs will suffice) for use in the integrated systems of the invention. Current art in software technology is adequate to allow implementation of the methods taught herein on a computer system. Thus, in specific embodiments, the present invention can comprise a set of logic instructions (either software, or hardware encoded instructions) for performing one or more of the methods as taught herein. For example, software for providing the data and/or statistical analysis can be constructed by one of skill using a standard programming language such as Visual Basic, Fortran, Basic, Java, or the like. Such software can also be constructed utilizing a variety of statistical programming languages, toolkits, or libraries.

FIG. 24 is a block diagram showing a representative example logic device in which various aspects of the present invention may be embodied. FIG. 24 shows an information appliance (or digital device) 700 that may be understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a computer system as illustrated in 700, containing CPU 707, optional input devices 709 and 711, disk drives 715 and optional monitor 705. Fixed media 717, or fixed media 722 over port 719, may be used to program such a system and may represent a disk-type optical or magnetic media, magnetic tape, solid state dynamic or static memory, etc. In specific embodiments, the invention may be embodied in whole or in part as software recorded on this fixed media. Communication port 719 may also be used to initially receive instructions that are used to program such a system and may represent any type of communication connection.

Various programming methods and algorithms, including genetic algorithms and neural networks, can be used to perform aspects of the data collection, correlation, and storage functions, as well as other desirable functions, as described herein. In addition, digital or analog systems such as digital or analog computer systems can control a variety of other functions such as the display and/or control of input and output files. Software for performing the electrical analysis methods of the invention are also included in the computer systems of the invention.

Optionally, the integrated systems of the invention include an automated workstation. For example, such a workstation can prepare and analyze samples by performing a sequence of events including: preparing samples from a tissue or blood sample; placing the samples into a microchamber array of the invention; and detecting cell or other reactions by optical, electrical or chemical measurements. The reaction data is digitized and recorded in the appropriate database.

Automated and/or semi-automated methods for solid and liquid phase high-throughput sample preparation and evaluation are available, and supported by commercially available devices. For example, robotic devices for preparation of cells. Alternatively, or in addition, robotic systems for liquid handling are available from a variety of sources, e.g., automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Beckman Coulter, Inc. (Fullerton, Calif.)) which mimic the manual operations performed by a scientist. Any of the above devices are suitable for use with the present invention, e.g., for high-throughput analysis of library components or subject samples. The nature and implementation of modifications to these devices (if any) so that they can operate as discussed herein will be apparent to persons skilled in the relevant art.

OTHER EMBODIMENTS

Although the present invention has been described in terms of various specific embodiments, it is not intended that the invention be limited to these embodiments. Modification within the spirit of the invention will be apparent to those skilled in the art.

It is understood that the examples and embodiments described herein are for illustrative purposes and that various modifications or changes in light thereof will be suggested by the teachings herein to persons skilled in the art and are to be included within the spirit and purview of this application and scope of the claims.

All publications, patents, and patent applications cited herein or filed with this submission, including any references filed as part of an Information Disclosure Statement, are incorporated by reference in their entirety.

What is claimed:

1. A method of fabricating a microculture microfluidic array, the method comprising:
   patterning fluidic structures in a first layer of a mold material by etching or electroplating metals on a silicon substrate, the first layer fluidic structures producing a fluidic resistance;
   etching or electroplating a pattern of fluidic structures in a second layer of a mold material adjacent to said first layer that are larger than the fluidic structures of the first layer, the fluidic structures of the second layer producing a fluidic resistance;
   introducing a settable elastomer or thermoplastic material into the mold and curing to form a main body of said array; and
   removing said array from said mold;
   wherein the fluidic resistance of the first layer fluidic structures is greater than the fluidic resistance of the second layer fluidic structures by a ratio in the range of about 10:1 to about 30:1.

2. The method of claim 1, wherein said patterning of fluidic structures in the first layer comprises:
   spinning a first layer of material on said substrate;
   defining a micro passage structure in said first layer; and
   wherein said patterning of fluidic structure in the second layer comprises;
   spinning a second layer of material on said first layer and said substrate;
   defining a plurality of culture microchambers and/or fluidic channels in said second layer;
   thereby producing a 2-level mold.

3. The method of claim 1, further comprising:
   providing a mold defining higher fluidic resistance passages and lower fluidic resistance areas;

injecting a settable plastic and/or polymer into said mold to form a molded microfluidic structure;

separating said mold from said molded structure; and attaching said molded structure to a cover piece to thereby form a microfluidic device with one or more microfluidic passages and/or channels and/or areas.

4. The method of claim 3, wherein:

said high fluidic resistance passages have a fluidic flow resistance ratio greater than about 10 to said lower fluidic resistance areas;

wherein said moldable material comprises a material selected from the group consisting of polydimethylsiloxane (PDMS), polymethylmethacrylate (PMMA), polycarbonate (PC), and polystyrene; and wherein said mold is constructed from a material selected from the group consisting of silicon, a polymer, a metal, and a metal alloy.

5. The method of claim 3, further comprising:

spin coating a layer of adhesive on a surface of said cover piece; and attaching said cover piece to the molded structure with said adhesive coating to form the microfluidic device.

6. The method of claim 3, wherein said cover piece is a material selected from the group of materials consisting of glass, a polymer and silicon.

* * * * *